US012486247B2

(12) United States Patent
Galán García et al.

(10) Patent No.: US 12,486,247 B2
(45) Date of Patent: Dec. 2, 2025

(54) COMPOUND AND AN ORGANIC SEMICONDUCTING LAYER, AN ORGANIC ELECTRONIC DEVICE, A DISPLAY DEVICE AND A LIGHTING DEVICE COMPRISING THE SAME

(71) Applicant: Novaled GmbH, Dresden (DE)

(72) Inventors: Elena Galán García, Dresden (DE); Benjamin Schulze, Dresden (DE); Domagoj Pavicic, Dresden (DE); Lidia Marin, Dresden (DE)

(73) Assignee: Novaled GmbH, Dresden (DE)

( * ) Notice: Subject to any disclaimer, the term of this patent is extended or adjusted under 35 U.S.C. 154(b) by 213 days.

(21) Appl. No.: 17/754,652

(22) PCT Filed: Oct. 8, 2020

(86) PCT No.: PCT/EP2020/078287

§ 371 (c)(1),
(2) Date: Apr. 7, 2022

(87) PCT Pub. No.: WO2021/069595

PCT Pub. Date: Apr. 15, 2021

(65) Prior Publication Data

US 2024/0132468 A1 Apr. 25, 2024

(30) Foreign Application Priority Data

Oct. 8, 2019 (EP) .................................... 19201931

(51) Int. Cl.
*C07D 401/10* (2006.01)
*C07D 239/74* (2006.01)
(Continued)

(52) U.S. Cl.
CPC ......... *C07D 401/10* (2013.01); *C07D 239/74* (2013.01); *C07D 241/12* (2013.01);
(Continued)

(58) Field of Classification Search
CPC .. C07D 401/10; C07D 239/74; C07D 241/12; C07D 251/22; C07D 413/14;
(Continued)

(56) References Cited

U.S. PATENT DOCUMENTS 6,437,123 B1 * 8/2002 Bock ...................... C09K 11/06 252/299.61
8,513,251 B2 * 8/2013 Taniguchi .............. A61P 25/00 514/252.05
(Continued)

FOREIGN PATENT DOCUMENTS

CN 105732294 A 7/2016
CN 107001292 A 8/2017
(Continued)

OTHER PUBLICATIONS

Chen et al., "Nitrogen heterocycle-containing materials for highly efficient phosphorescent OLEDs with low operating voltage", Journal of Materials Chemistry, Oct. 2014 (Year: 2014).*
(Continued)

*Primary Examiner* — Caleb E Henry
(74) *Attorney, Agent, or Firm* — Eversheds Sutherland (US) LLP

(57) ABSTRACT

The present invention relates to compound having the following Formula (I) a semiconducting layer comprising this compound, an organic electronic device comprising said
(Continued)

organic semiconducting layer, as well as to a device comprising the organic electronic device.

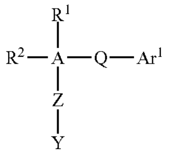

(I)

13 Claims, 2 Drawing Sheets

(51) Int. Cl.

| | |
|---|---|
| ***C07D 241/12*** | (2006.01) |
| ***C07D 251/22*** | (2006.01) |
| ***C07D 413/14*** | (2006.01) |
| ***H10K 50/165*** | (2023.01) |
| ***H10K 85/60*** | (2023.01) |

(52) U.S. Cl.

CPC ......... *C07D 251/22* (2013.01); *C07D 413/14* (2013.01); *H10K 50/165* (2023.02); *H10K 85/615* (2023.02); *H10K 85/654* (2023.02); *H10K 85/6574* (2023.02)

(58) Field of Classification Search

CPC .. C07D 401/04; C07D 403/04; C07D 251/10; C07D 239/70; C07D 241/42; C07D 251/24; C07D 405/14; C07D 471/04; C07D 307/91; C07D 333/76; H10K 50/165; H10K 85/615; H10K 85/654; H10K 85/6574; H10K 85/6572; H10K 85/624; H10K 85/626; H10K 85/6576; H10K 50/11; Y02E 10/549; C07C 13/72; C07C 2603/18; C07C 2603/24; C07C 2603/26; C07C 2603/97; C07C 255/35; C07C 2603/40; C07C 255/34; C07C 255/37; C09K 11/06; C09K 2211/1007; C09K 2211/1011; C09K 2211/1018; H01L 51/0054; H01L 51/5036; H01L 51/506; H01L 51/5088; H01L 51/0051; H01L 51/0059; H01L 51/0072; H01L 51/5278

See application file for complete search history.

(56) References Cited

U.S. PATENT DOCUMENTS

| | | | | |
|---|---|---|---|---|
| 8,927,559 | B2 * | 1/2015 | Aslanian | C07D 405/10 514/266.3 |
| 10,596,163 | B2 * | 3/2020 | Chen | C07D 403/04 |
| 11,177,441 | B2 * | 11/2021 | Han | C09K 11/06 |
| 2004/0254212 | A1 * | 12/2004 | Denholm | A61P 37/08 546/122 |
| 2008/0312236 | A1 * | 12/2008 | Leblond | C07D 265/30 546/276.4 |
| 2012/0277430 | A1 * | 11/2012 | Taniguchi | A61P 43/00 544/238 |
| 2016/0095858 | A1 * | 4/2016 | Miller | C07D 403/10 546/261 |
| 2017/0040547 | A1 * | 2/2017 | Chen | C07D 251/24 |
| 2018/0243298 | A1 * | 8/2018 | Black | C07D 417/12 |
| 2019/0140186 | A1 * | 5/2019 | Schulze | H10K 85/654 |
| 2019/0140187 | A1 * | 5/2019 | Schulze | H10K 85/615 |
| 2019/0319196 | A1 * | 10/2019 | Sim | C07D 403/10 |
| 2019/0319197 | A1 * | 10/2019 | Pan | C07D 209/86 |
| 2020/0095226 | A1 * | 3/2020 | Pan | H10K 85/654 |
| 2020/0361916 | A1 * | 11/2020 | Schulze | C07D 405/14 |
| 2021/0070717 | A1 * | 3/2021 | Li | H10K 85/00 |
| 2021/0328151 | A1 * | 10/2021 | Zhuang | H10K 85/626 |
| 2022/0344588 | A1 * | 10/2022 | Yu | C09K 11/02 |
| 2023/0002346 | A1 * | 1/2023 | Rawling | C07D 405/04 |

FOREIGN PATENT DOCUMENTS

| | | | |
|---|---|---|---|
| CN | 107721979 | A | 2/2018 |
| CN | 107827826 | A | 3/2018 |
| CN | 108431980 | A | 8/2018 |
| CN | 108997239 | | 12/2018 |
| CN | 108997239 | A | 12/2018 |
| CN | 109535093 | A | 3/2019 |
| CN | 114222736 | A | 3/2022 |
| EP | 3287505 | A1 | 2/2018 |
| EP | 3312896 | A1 | 4/2018 |
| EP | 3412751 | A1 | 12/2018 |
| EP | 3502106 | A1 | 6/2019 |
| EP | 3527558 | A1 | 8/2019 |
| EP | 3670504 | A1 | 6/2020 |
| EP | 3766875 | A1 | 1/2021 |
| JP | 2018121046 | A | 8/2018 |
| JP | 2018526358 | A | 9/2018 |
| JP | 2019019126 | A | 2/2019 |
| JP | 6902859 | B2 | 7/2021 |
| JP | 7063407 | B2 | 5/2022 |
| KR | 20180093354 | | 8/2018 |
| KR | 20180093354 | A | 8/2018 |
| KR | 20190053562 | A | 5/2019 |
| WO | 2012079678 | A1 | 6/2012 |
| WO | 2013073859 | A1 | 5/2013 |
| WO | 2019166206 | A1 | 9/2019 |
| WO | 2020/126972 | A1 | 6/2020 |
| WO | 2020126972 | | 6/2020 |

OTHER PUBLICATIONS

European Patent Office, International Search Report and Written Opinion issued in international application humber PCT/EP2020/078287, dated Apr. 15, 2021, 9 pp.

Communication pursuant to Rule 114(2) EPC issued in European application No. 19201931.3, dated May 17, 2024 (17 pages).

Communication pursuant to Rule 114(2) EPC issued in European application No. 20789574.9, dated May 24, 2024 (357 pages).

Decision of Rejection issued in Chinese application No. 202080070326.5, dated Nov. 22, 2024 (30 pages).

European Patent Office, Communication pursuant to Rule 114(2) EPC, Observations by a third party issued in corresponding European application No. 19201931.3, dated Oct. 4, 2021, 13 pp.

Notice of Reasons for Refusal issued in Japan application No. 2022-521153, dated Jul. 6, 2024 (11 pages).

Notification of First Office Action issued in China application No. 202080070326.5, dated Oct. 11, 2023 (30 pages).

Written Opinion of the International Searching Authority for PCT/EP2020/078287, Apr. 15, 2021.

Notice to File a Response issued in Korean application No. 10-2022-7015212, dated Feb. 19, 2025 (21 pages).

* cited by examiner

COMPOUND AND AN ORGANIC SEMICONDUCTING LAYER, AN ORGANIC ELECTRONIC DEVICE, A DISPLAY DEVICE AND A LIGHTING DEVICE COMPRISING THE SAME

CROSS-REFERENCE TO RELATED APPLICATIONS

This application is a U.S. national phase application of PCT/EP2020/078287, filed Oct. 8, 2020, which claims priority to European Patent Application No. 19201931.3, filed Oct. 8, 2019. The content of these applications is incorporated by reference herein.

The present invention relates to a compound as well as to an organic semiconducting layer comprising the same. The invention further relates to an organic electronic device comprising the organic semiconducting layer, respectively the compound. Furthermore, the invention is related to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed from organic and/or organometallic compounds.

When a voltage is applied to the anode and the cathode, holes injected from the anode electrode move to the EML, via the HTL, and electrons injected from the cathode electrode move to the EML, via the ETL. The holes and electrons recombine in the EML to generate excitons. When the excitons drop from an excited state to a ground state, light is emitted. The injection and flow of holes and electrons should be balanced, so that an OLED having the above-described structure has excellent efficiency.

Compounds comprising N-containing heteroaryl groups, triazine groups, are known in the art and used in organic electronics applications, especially as electron transport materials.

However, there is still a need to improve the electronic properties of respective compounds for use in organic electronic devices, in particular to provide compounds having an improved vacuum processability compared to compounds known in the art. Furthermore, there is still a need to provide compounds suitable to improve the performance of organic electronic devices, in particular to improve efficiency, lifetime and driving voltage thereof, in particular with respect to the lifetime.

It is therefore an object of the present invention to provide novel organic electronic devices and compounds for use therein overcoming drawbacks of the prior art, in particular to provide novel compounds having improved properties, in particular vacuum processability, and which may be suitable to improve the lifetime and stability of organic electronic devices, in particular when used in an electron transport layer thereof.

SUMMARY OF THE INVENTION

The above object is achieved by a Compound having the general Formula (I)

(I)

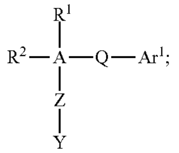

wherein

A is substituted or unsubstituted $C_3$ to $C_{14}$ heteroarylene comprising at least one six-membered ring, the six-membered ring comprising at least two N-atoms, wherein the one or more substituents, if present in the group A, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^1$, $R^2$, Q-$Ar^1$ and Z—Y are bound to C-atoms of A;

Q-$Ar^1$ and Z—Y are bound to C-atoms of the six-membered ring comprising at least two N-atoms of A;

$R^1$ is selected from the group consisting of H, substituted or unsubstituted $C_6$ to $C_{18}$ aryl, preferably phenyl, naphtyl or biphenyl, most preferred phenyl, and substituted or unsubstituted $C_2$ to $C_{18}$ heteroaryl, preferably substituted or unsubstituted $C_5$ to $C_{12}$ heteroaryl, most preferred pyridyl, dibenzofuranyl, dibenzothiophene-yl, or benzothiophene-yl, wherein the one or more substituents, if present in the group $R^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^2$ is selected from the group consisting of H, substituted or unsubstituted $C_6$ to $C_{18}$ aryl, preferably phenyl, naphtyl or biphenyl, most preferred phenyl, and substituted or unsubstituted $C_2$ to $C_{18}$ heteroaryl, preferably substituted or unsubstituted $C_5$ to $C_{12}$ heteroaryl, most preferred pyridyl, dibenzofuranyl, dibenzothiophene-yl, or benzothiophene-yl, wherein the one or more substituents, if present in the group $R^2$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN; or is absent in case that A is $C_3$ heteroarylene;

Q represents a single bond between A and $Ar^1$ or a group having the Formula (II) or (III)

(II)

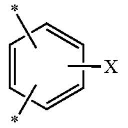

(III)

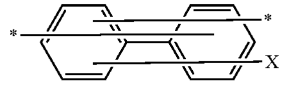

in Formulas (II) and (III) the "*" symbols represent the positions for binding to A and $Ar^1$, respectively;

X is H, $C_1$ to $C_7$ alkyl or is represented by the general formula (IV)

(IV)

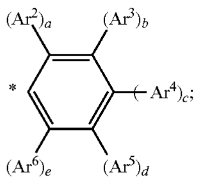

in formula (IV)

at least two of $Ar^2$ to $Ar^6$ are in ortho-position to each other; and/or at least one of $Ar^2$ and $Ar^6$ is in ortho-position to the *-position; or in case that a to e are 0 at the same time, X is in ortho-position to $Ar^1$;

$Ar^1$ is selected from the group consisting of substituted or unsubstituted $C_6$ to $C_{60}$ aryl, CN-substituted phenyl and substituted or unsubstituted N-containing $C_3$ to $C_{20}$ heteroaryl, wherein the one or more substituents, if present in the group $Ar^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$Ar^1$ is different from A;

Z represents a single bond between A and Y or a group having the Formula (V) or (VI)

(V)

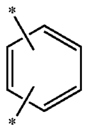

(VI)

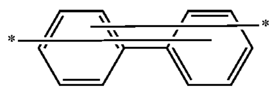

in Formulas (V) and (VI) the "*" symbols represent the positions for binding to A and Y, respectively;

Y is H, $C_1$ to $C_7$ alkyl or is represented by the general formula (VII)

(VII)

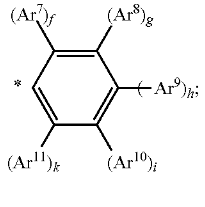

in formula (VII)

at least two of $Ar^7$ to $Ar^{11}$ are in ortho-position to each other; and/or at least one of $Ar^7$ and $Ar^{11}$ is in ortho-position to the *-position;

X and Y cannot be H and/or $C_1$ to $C_7$ alkyl at the same time;

Q and Y may be substituted with one or more substituents selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

a to k are independently 0 or 1, provided that $2 \leq a+b+c+d+e+f+g+h+i+k \leq 5$;

$Ar^2$ to $Ar^{11}$ are independently selected from the group consisting of substituted or unsubstituted $C_6$ to $C_{12}$ aryl and $C_4$ to $C_{10}$ heterorayl, wherein the one or more substituents, if present in one or more of the groups $Ar^2$ to $Ar^{11}$, are independently selected from the group consisting of $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F and CN;

neither Formula (IV) nor Formula (VII) comprises condensed aromatic rings; and a compound having the following formula is excluded

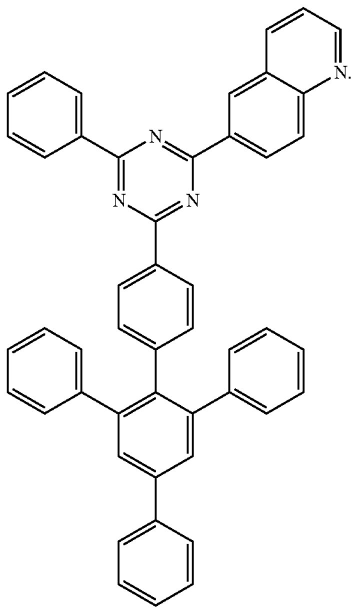 [SMILES: c1ccc(-c2cc(-c3ccccc3)c(-c3ccc(-c4nc(-c5ccccc5)nc(-c5ccc6ncccc6c5)n4)cc3)c(-c3ccccc3)c2)cc1]

It was surprising found by the inventors that compounds of Formula (I) above have a vacuum processability which is improved compared to compounds known in the art. Furthermore, it was surprisingly found that organic electronic devices comprising such compounds show improved performance, in particular show improved lifetime and operating voltage stability.

The improvements with respect to vacuum processability and (at the same time) improved lifetime and operating voltage stability were surprisingly found to be even more pronounced for the preferred embodiments mentioned below, wherein the best effects were achieved when combining two or more of the preferred embodiments.

The inventive compound is represented by the general Formula (I)

(I)

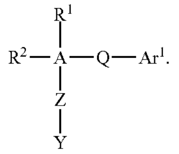

In the Formula (I) A is substituted or unsubstituted $C_3$ to $C_{14}$ heteroarylene comprising (at least) one six-membered ring. The six-membered ring comprising at least two N-atoms. In this regard, it may be provided that A comprises besides the 6-membered ring which comprises the at least two N-atoms one or more further rings, preferably aromatic rings, even more preferred 6-membered aromatic rings, not containing further heteroatoms, in particular no further N-atoms. It may be provided that A comprises in "the six-membered ring comprising at least two N-atoms" 2 or 3 N-atoms.

A may be selected from the group consisting of triazinylene, diazinylene, pyrimidinylene, pyrazinylene, quinoxalinyl, quinazolinylene, and benzoquinazolinylene.

Preferred groups A are the following groups

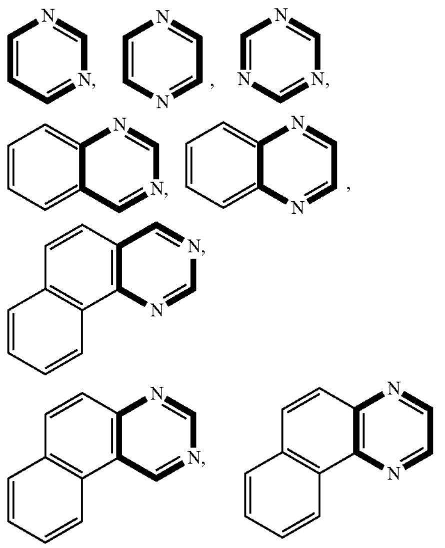

wherein the bold-printed part of the respective group is the 6-membered ring comprising at least two N-atoms.

In particular preferred are groups A which have a calculated LUMO entry level between −1.50 eV and 2.00 eV, even more preferred between −1.55 eV and −1.90 eV, when in the molecular calculations the bonding positions of the 6-membered ring comprising at least two N-atoms are occupied by phenyl rings. This is shown in Table 4.

The one or more substituents, if present in the group A, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN.

$R^1$, $R^2$, Q-$Ar^1$ and Z—Y are bound to C-atoms of A. Q-$Ar^1$ and Z—Y are bound to C-atoms of the six-membered ring comprising at least two N-atoms of A. For example, if A is

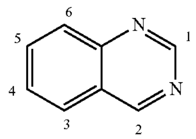

Q-$Ar^1$ and Z—Y are bound to the positions 1 and 2 while $R^1$ and $R^2$ are bound to a position 3 to 6, respectively.

$R^1$ and $R_2$ are independently selected from the group consisting of H, substituted or unsubstituted $C_6$ to $C_{18}$ aryl, preferably phenyl, naphtyl or biphenyl, most preferred phenyl, and substituted or unsubstituted $C_2$ to $C_{18}$ heteroaryl, preferably substituted or unsubstituted $C_5$ to $C_{12}$ heteroaryl, most preferred pyridyl, dibenzofuranyl, dibenzothiophene-yl, or benzothiophene-yl.

The one or more substituents, if present in the group $R^1$ and/or $R^2$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN.

If A is $C_3$ heteroarylene then $R^2$ is absent in the Formula (I). For example, if A is

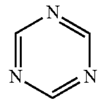

the compound of Formula (I) has the structure

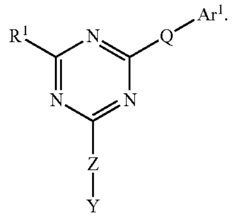

Q represents a single bond between A and $Ar^1$ or is a group having the Formula (II) or (III)

(II)

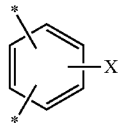

(III)

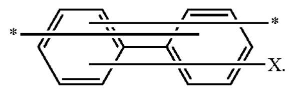

In the above Formulas (II) and (III) the "*" and the X may be bound to any of the carbon atoms of the phenylene, respectively the biphenylene moiety, as long as it is, of course, provided that the different "*" and the X are not bound to the same atom.

In Formulas (II) and (III) the "*" symbols represent the positions for binding to A and $Ar^1$, respectively.

X is H, $C_1$ to $C_7$ alkyl or is represented by the general formula (IV)

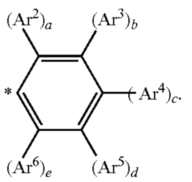

(IV)

In the Formula (IV) the "*" symbol represents the binding position to the group Q or, in case that Q is a single bond, to the group A.

In formula (IV) at least two of $Ar^2$ to $Ar^6$ are in ortho-position to each other; and/or at least one of $Ar^2$ and $Ar^6$ is in ortho-position to the *-position. Alternatively, in case that a to e are 0 at the same time, X is in ortho-position to $Ar^1$.

Referring to the case that "at least two of $Ar^2$ to $Ar^6$ are in ortho-position to each other", for example $Ar^2$ and $Ar^3$ are in ortho-position to each other, i.e. the Formula (IV) may in this case have the formula

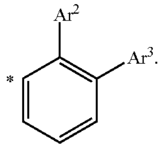

In the case "at least one of $Ar^2$ and $Ar^6$ is in ortho-position to the *-position" the Formula (IV) may be as follows

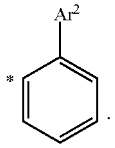

In the case "a to e are 0 at the same time, X is in ortho-position to $Ar^1$" the moiety Q-$Ar^1$ is as follows

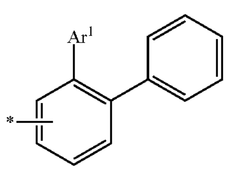

wherein the remaining "*" is the binding position to the A which may be at any of the free positions of Q.

$Ar^1$ is selected from the group consisting of CN-substituted phenyl and substituted or unsubstituted N-containing $C_3$ to $C_{20}$ heteroaryl. The CN-substituted phenyl may be further substituted.

The CN-substituted phenyl may be

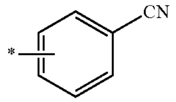

wherein "*" is the binding position to Q.

In case that $Ar^1$ is substituted or unsubstituted aryl, it may be provided that the aryl contains at least 6 carbon atoms, alternatively at least 7 carbon atoms, alternatively at least 8 carbon atoms, alternatively at least 9 carbon atoms, alternatively at least 10 carbon atoms, alternatively at least 11 carbon atoms, alternatively at least 12 carbon atoms, alternatively at least 13 carbon atoms, alternatively at least 14 carbon atoms, alternatively at least 15 carbon atoms, alternatively at least 16 carbon atoms, alternatively at least 17 carbon atoms, alternatively at least 18 carbon atoms, alternatively at least 19 carbon atoms, alternatively at least 20 carbon atoms, alternatively at least 21 carbon atoms, alternatively at least 22 carbon atoms, alternatively at least 23 carbon atoms, alternatively at least 24 carbon atoms, alternatively at least 25 carbon atoms, alternatively at least 26 carbon atoms, alternatively at least 27 carbon atoms, alternatively at least 28 carbon atoms, alternatively at least 29 carbon atoms, alternatively at least 30 carbon atoms, alternatively at least 31 carbon atoms, alternatively at least 32 carbon atoms, alternatively at least 33 carbon atoms, alternatively at least 34 carbon atoms, alternatively at least 35 carbon atoms, alternatively at least 36 carbon atoms, alternatively at least 37 carbon atoms, alternatively at least 38 carbon atoms, alternatively at least 39 carbon atoms, alternatively at least 40 carbon atoms, alternatively at least 41 carbon atoms, alternatively at least 42 carbon atoms, alternatively at least 43 carbon atoms, alternatively at least 44 carbon atoms, alternatively at least 45 carbon atoms, alternatively at least 46 carbon atoms, alternatively at least 47 carbon atoms, alternatively at least 48 carbon atoms, alternatively at least 49 carbon atoms, alternatively at least 50 carbon atoms, alternatively at least 51 carbon atoms, alternatively at least 52 carbon atoms, alternatively at least 53 carbon atoms, alternatively at least 54 carbon atoms, alternatively at least 55 carbon atoms, alternatively at least 56 carbon atoms, alternatively at least 57 carbon atoms, alternatively at least 58 carbon atoms, alternatively at least 59 carbon atoms.

In the above paragraph, the number of carbon atoms in $Ar^1$ does not include the number of carbon atoms in the substituents of $Ar^1$, if present.

In case that $Ar^1$ is substituted or unsubstituted aryl, it may be provided that the aryl contains not more than 60 carbon atoms, alternatively not more than 59 carbon atoms, alternatively not more than 58 carbon atoms, alternatively not more than 57 carbon atoms, alternatively not more than 56 carbon atoms, alternatively not more than 55 carbon atoms, alternatively not more than 54 carbon atoms, alternatively not more than 53 carbon atoms, alternatively not more than 52 carbon atoms, alternatively not more than 51 carbon atoms, alternatively not more than 50 carbon atoms, alternatively not more than 49 carbon atoms, alternatively not more than 48 carbon atoms, alternatively not more than 47 carbon atoms, alternatively not more than 46 carbon atoms, alternatively not more than 45 carbon atoms, alternatively not more than 44 carbon atoms, alternatively not more than 43 carbon atoms, alternatively not more than 42 carbon atoms, alternatively not more than 41 carbon atoms, alternatively not more than 40 carbon atoms, alternatively not more than 39 carbon atoms, alternatively not more than 38 carbon atoms, alternatively not more than 37 carbon atoms, alternatively not more than 36 carbon atoms, alternatively not more than 35 carbon atoms, alternatively not more than 34 carbon atoms, alternatively not more than 33 carbon atoms, alternatively not more than 32 carbon atoms, alternatively not more than 31 carbon atoms, alternatively not more than 30 carbon atoms, alternatively not more than 29 carbon atoms, alternatively not more than 28 carbon atoms, alternatively not more than 27 carbon atoms, alternatively not more than 26 carbon atoms, alternatively not more than 25 carbon atoms, alternatively not more than 24 carbon atoms, alternatively not more than 23 carbon atoms, alternatively not more than 22 carbon atoms, alternatively not more than 21 carbon atoms, alternatively not more than 20 carbon atoms, alternatively not more than 19 carbon atoms, alternatively not more than 18 carbon atoms, alternatively not more than 17 carbon atoms, alternatively not more than 16 carbon atoms, alternatively not more than 15 carbon atoms, alternatively not more than 14 carbon atoms, alternatively not more than 13 carbon atoms, alternatively not more than 12 carbon atoms, alternatively not more than 11 carbon atoms, alternatively not more than 10 carbon atoms, alternatively not more than 9 carbon atoms, alternatively not more than 8 carbon atoms, alternatively not more than 7 carbon atoms, alternatively not more than 6 carbon atoms.

In the above paragraph, the number of carbon atoms in $Ar^1$ does not include the number of carbon atoms in the substituents of $Ar^1$, if present.

$Ar^1$ may be selected from substituted or unsubstituted $C_6$ to $C_{54}$ aryl, CN-substituted phenyl and substituted or unsubstituted N-containg $C_3$ to $C_{20}$ heteroaryl; substituted or unsubstituted $C_6$ to $C_{42}$ aryl, CN-substituted phenyl and substituted or unsubstituted N-containg $C_3$ to $C_{20}$ heteroaryl; substituted or unsubstituted $C_6$ to $C_{36}$ aryl, CN-substituted phenyl and substituted or unsubstituted N-containg $C_3$ to $C_{20}$ heteroaryl; substituted or unsubstituted $C_6$ to $C_{30}$ aryl, CN-substituted phenyl and substituted or unsubstituted N-containg $C_3$ to $C_{20}$ heteroaryl; substituted or unsubstituted $C_6$ to $C_{24}$ aryl, CN-substituted phenyl and substituted or unsubstituted N-containg $C_3$ to $C_{20}$ heteroaryl; substituted or unsubstituted $C_6$ to $C_{18}$ aryl, CN-substituted phenyl and substituted or unsubstituted N-containg $C_3$ to $C_{15}$ heteroaryl; substituted or unsubstituted $C_6$ to $C_{12}$ aryl, CN-substituted phenyl and substituted or unsubstituted N-containg $C_3$ to $C_{15}$ heteroaryl; substituted or unsubstituted $C_{12}$ to $C_{18}$ aryl, CN-substituted phenyl and substituted or unsubstituted N-containg $C_3$ to $C_{15}$ heteroaryl.

$Ar^1$ may be selected from the group consisting of phenyl, naphthyl, anthracenyl, phenanthrenyl, o-terphenyl, m-terphenyl, p-terphenyl, phenalenyl, pyrenyl, tetracenyl, chrysenyl, perylenyl, benzofluoranthenyl, anthanthrenyl, pentacenyl, pentaphenyl, fluorenyl, spiro-fluorenyl, triphenylyl, fluoranthenyl.

$Ar^1$ may be selected from the group consisting of pyridinyl, quinolinyl, isoquinolinyl, benzoquinolinyl, azaphenanthrenyl, quinazolinyl, benzoquinazolinyl, pyrimidinyl, pyrazinyl, triazinyl, benzimidazolyl, benzothiazolyl, dibenzothiazolyl, benzofuranyl, dibenzofuranyl, benzo[4,5]thieno[3,2-d]pyrimidinyl, carbazolyl, xanthenyl, spiro-xanthenyl, phenoxazinyl, benzoacridinyl, dibenzoacridinyl, benzo-nitrilyl.

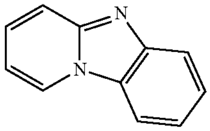

, and

-continued

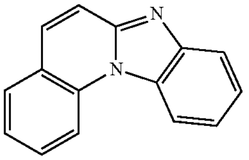

.

In case $Ar^1$ is substituted the one or more substituents, if present in the group $Ar^1$, may be independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN.

$Ar^1$ may be selected from the group consisting of phenyl, naphthyl, phenanthrene, pyridinyl, quinolinyl, isoquinolinyl, azaphenanthrenyl, carbazolyl, benzo-nitrilyl,

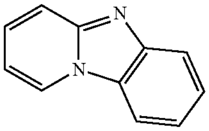

, and

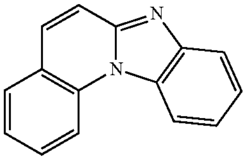

.

The one or more substituents, if present in the group $Ar^1$, are independently selected from the group consisting of $C_1$ to $C_7$ alkyl, $C_1$ to $C_7$ alkoxy, partially or perdeuterated $C_1$ to $C_7$ alkyl, partially or perdeuterated Ct to $C_7$ alkoxy, partially or perfluorinated $C_1$ to $C_7$ alkyl, partially or perfluorinated $C_1$ to $C_7$ alkoxy, D, F and CN.

$Ar^1$ is different from A. That is, in case that $Ar^1$ substituted or unsubstituted N-containing $C_3$ to $C_{20}$ heteroaryl this group is not the same $C_3$ to $C_{20}$ heteroaryl as selected for A. It may be provided (but not necessarily) that $Ar^1$ is a $C_3$ to $C_{20}$ heteroaryl containing only one N-atom, for example

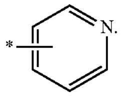

Z represents a single bond between A and Y or a group having the Formula (V) or (VI)

(V)

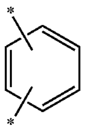

(VI)

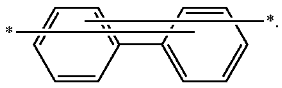

In the above Formulas (V) and (VI) the "*" may be bound to any of the carbon atoms of the phenylene, respectively the biphenylene moiety, as long as it is, of course, provided that the different "*" are not at the same atom.

In Formulas (V) and (VI) the "*" symbols represent the positions for binding to A and Y, respectively.

Y is H, $C_1$ to $C_7$ alkyl or is represented by the general formula (VII)

(VII)

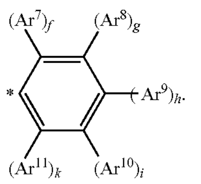

In formula (VII) at least two of $Ar^7$ to $Ar^{11}$ are in ortho-position to each other; and/or at least one of $Ar^7$ and $Ar^{11}$ is in ortho-position to the *-position.

Referring to the case that "at least two of $Ar^7$ to $Ar^{11}$ are in ortho-position to each other", for example $Ar^7$ to $Ar^{11}$ are in ortho-position to each other, i.e. the Formula (VII) may in this case have the formula

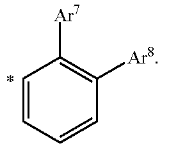

In the case "at least one of $Ar^7$ and $Ar^{11}$ is in ortho-position to the *-position" the Formula (VII) may be as follows

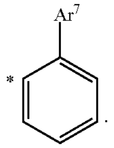

The compound of Formula (I) possesses at least one ortho-position.

X and Y cannot be H and/or $C_1$ to $C_7$ alkyl at the same time. That is, at least one of X and Y has the formula (IV) (in case of X) or the formula (VII) (in case of Y). Likewise, it may be provided that at the same time X has the formula (IV) and Y has the formula (VII)—wherein the further limitations with respect to the inventive compounds have to be observed.

Q and Z may be substituted with one or more substituents selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN.

a to k are independently 0 or 1, provided that $2 \leq a+b+c+d+e+f+g+h+i+k \leq 5$. It may further be provided that the total number of aromatic rings comprised in the compound of Formula (I) is from 7 to 14, alternatively 8 to 12, alternatively 8 to 11. In this regard, it may be provided that if X gets larger than Y gets smaller, and vice versa. It may further be provided that if the number of aromatic rings increases in one or both of the groups Q and Z than X and Y get smaller, and vice versa.

For example if the group having the Formula (VII) has the structure

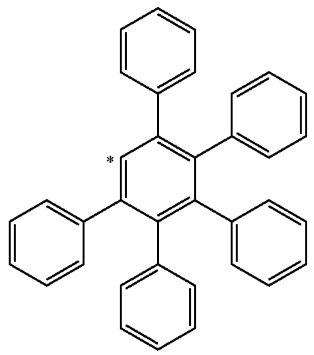 [SMILES: c1ccc(-c2cc(-c3ccccc3)c(-c3ccccc3)c(-c3ccccc3)c2-c2ccccc2)cc1]

it is at the same time provided that the group having the formula (IV) is

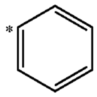

and Q and Z may be single bonds to keep the total number of aromatic rings in the compound of Formula (I) low.

If, in another example, both Formula (IV) as well as Formula (VII) have the structure

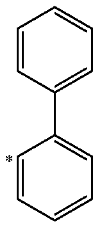 [SMILES: c1ccc(-c2ccccc2)cc1]

then it may be provided that Q and Z are aromatic groups, such as phenylene, to ensure a sufficient number of aromatic rings. In this regard, however, also the number of aromatic rings already comprised in the group A, the group $R^1$ etc. has to be kept into consideration. By balancing the total number of aromatic rings in Formula (I), particular good vacuum processability may be achieved.

$Ar^2$ to $Ar^{11}$ are independently selected from the group consisting of substituted or unsubstituted $C_6$ to $C_{12}$ aryl and $C_4$ to $C_{10}$ heteroaryl.

The one or more substituents, if present in one or more of the groups $Ar^2$ to $Ar^{11}$, are independently selected from the group consisting of $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F and CN.

Neither Formula (IV) nor Formula (VII) comprises condensed aromatic rings. The term "condensed aromatic rings" refers to an aryl group comprising at least two aromatic rings which are fused to each other by sharing two carbon atoms with each other, such as, for example, naphthyl. In this regard, it may be provided that the condensed aryl group (or the condensed arylene group) comprises more than two fused rings wherein each of the rings is fused with at least one other aryl ring of the condensed aryl(ene) by sharing with this one (or more) further ring(s) two carbon atoms. Non-limiting examples of such condensed aryl groups are fluoranthenyl, chrysenyl, pyrenyl etc.

A compound having the following formula is excluded from the scope of the invention

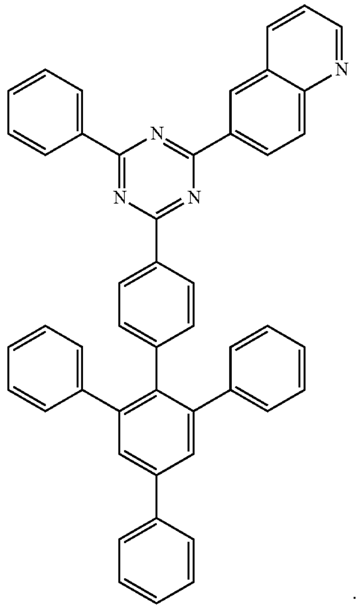 [SMILES: c1ccc(-c2cc(-c3ccccc3)c(-c3ccc(-c4nc(-c5ccccc5)nc(-c5ccc6ncccc6c5)n4)cc3)c(-c3ccccc3)c2)cc1]

Q may represent a group having the Formula (II) or (III) and/or Z represents a group having the Formula (V) or (VI). Q may represent a group having the Formula (II) and/or Z represents a group having the Formula (V). Q may represent a group having the Formula (II) and Z represents a group having the Formula (V).

In an embodiment, the compound of Formula (I) has a calculated molecular dipole moment of larger than 0.9 Debye, further preferred larger than 1.1 Debye.

In one preferred embodiment, a compound having the general Formula (I) is provided (I)

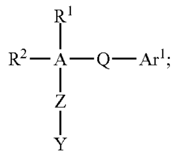

wherein

A is substituted or unsubstituted $C_3$ to $C_{14}$ heteroarylene comprising at least one six-membered ring, the six-membered ring comprising at least two N-atoms, wherein the one or more substituents, if present in the group A, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^1$, $R^2$, Q-$Ar^1$ and Z—Y are bound to C-atoms of A;

Q-$Ar^1$ and Z—Y are bound to C-atoms of the six-membered ring comprising at least two N-atoms of A;

$R^1$ is selected from the group consisting of H, phenyl, naphtyl or biphenyl, most preferred phenyl, wherein the one or more substituents, if present in the group $R^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^2$ is selected from the group consisting of H, phenyl, naphtyl or biphenyl, most preferred phenyl, wherein the one or more substituents, if present in the group $R^2$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN; or is absent in case that A is $C_3$ heteroarylene;

Q represents a single bond between A and $Ar^1$ or a group having the Formula (II) or (III)

(II)

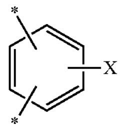

(III)

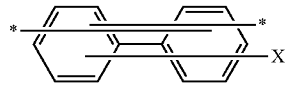

in Formulas (II) and (III) the "*" symbols represent the positions for binding to A and $Ar^1$, respectively;

X is H, $C_1$ to $C_7$ alkyl or is represented by the general formula (IV)

(IV)

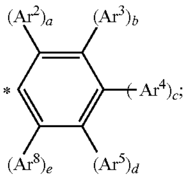

in formula (IV)

at least two of $Ar^2$ to $Ar^6$ are in ortho-position to each other; and/or at least one of $Ar^2$ and $Ar^6$ is in ortho-position to the *-position; or in case that a to e are 0 at the same time, X is in ortho-position to $Ar^1$;

$Ar^1$ is selected from the group consisting of substituted or unsubstituted $C_6$ to Cis aryl, CN-substituted phenyl and substituted or unsubstituted N-containg $C_3$ to $C_{15}$ heteroaryl, wherein the one or more substituents, if present in the group $Ar^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$Ar^1$ is different from A;

Z represents a single bond between A and Y or a group having the Formula (V) or (VI)

(V)

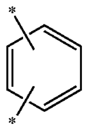

(VI)

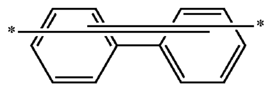

in Formulas (V) and (VI) the "*" symbols represent the positions for binding to A and Y, respectively;

Y is H, $C_1$ to $C_7$ alkyl or is represented by the general formula (VII)

(VII)

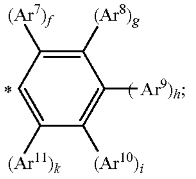

in formula (VII)

at least two of $Ar^7$ to $Ar^{11}$ are in ortho-position to each other; and/or at least one of $Ar^7$ and $Ar^{11}$ is in ortho-position to the *-position;

X and Y cannot be H and/or $C_1$ to $C_7$ alkyl at the same time;

Q and Z may be substituted with one or more substituents selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

a to k are independently 0 or 1, provided that $2 \leq a+b+c+d+e+f+g+h+i+k \leq 5$;

$Ar^2$ to $Ar^{11}$ are independently selected from the group consisting of substituted or unsubstituted $C_6$ to $C_{12}$ aryl and $C_4$ to $C_{10}$ heteroaryl, wherein the one or more substituents, if present in one or more of the groups $Ar^2$ to $Ar^{11}$, are independently selected from the group consisting of $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F and CN;

neither Formula (IV) nor Formula (VII) comprises condensed aromatic rings; and a compound having the following formula is excluded

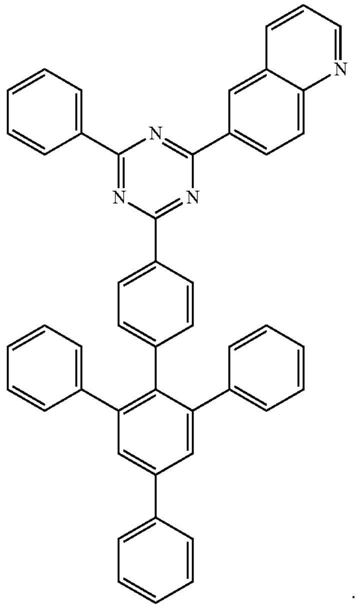 [SMILES: c1ccc(-c2cc(-c3ccccc3)c(-c3ccc(-c4nc(-c5ccccc5)nc(-c5ccc6ncccc6c5)n4)cc3)c(-c3ccccc3)c2)cc1]

In one preferred embodiment, a compound having the general Formula (I) is provided (I)

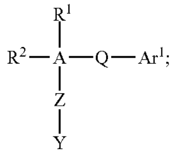

wherein

A is substituted or unsubstituted $C_3$ to $C_{14}$ heteroarylene comprising at least one six-membered ring, the six-membered ring comprising at least two N-atoms, wherein the one or more substituents, if present in the group A, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^1$, $R^2$, Q-$Ar^1$ and Z—Y are bound to C-atoms of A;

Q-$Ar^1$ and Z—Y are bound to C-atoms of the six-membered ring comprising at least two N-atoms of A;

$R^1$ is selected from the group consisting of H, and substituted or unsubstituted $C_6$ to $C_8$ aryl, preferably phenyl, naphtyl or biphenyl, most preferred phenyl, wherein the one or more substituents, if present in the group $R^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^2$ is selected from the group consisting of H, and substituted or unsubstituted $C_6$ to $C_{18}$ aryl, preferably phenyl, naphtyl or biphenyl, most preferred phenyl, wherein the one or more substituents, if present in the group $R^2$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN; or is absent in case that A is $C_3$ heteroarylene;

Q represents a single bond between A and $Ar^1$ or a group having the Formula (II) or (III)

(II)

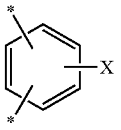

(III)

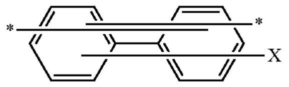

in Formulas (II) and (III) the "*" symbols represent the positions for binding to A and $Ar^1$, respectively;

X is H, $C_1$ to $C_7$ alkyl or is represented by the general formula (IV)

(IV)

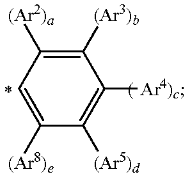

in formula (IV)

at least two of $Ar^2$ to $Ar^6$ are in ortho-position to each other; and/or at least one of $Ar^2$ and $Ar^6$ is in ortho-position to the *-position; or in case that a to e are 0 at the same time, X is in ortho-position to $Ar^1$;

$Ar^1$ is substituted or unsubstituted and selected from the group consisting of phenyl, naphthyl, phenanthrene, pyridinyl, quinolinyl, isoquinolinyl, azaphenanthrenyl, carbazolyl, benzo-nitrilyl,

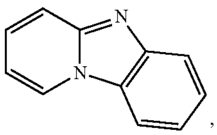

, and

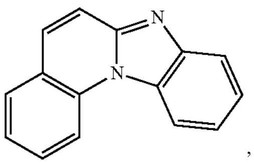

, wherein the one or more substituents, if present in the group $Ar^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$Ar^1$ is different from A;

Z represents a single bond between A and Y or a group having the Formula (V) or (VI)

(V)

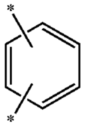

(VI)

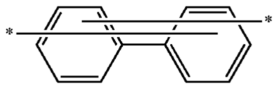

in Formulas (V) and (VI) the "*" symbols represent the positions for binding to A and Y, respectively;

Y is H, $C_1$ to $C_7$ alkyl or is represented by the general formula (VII)

(VII)

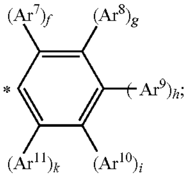

in formula (VII)

at least two of $Ar^7$ to $Ar^{11}$ are in ortho-position to each other; and/or at least one of $Ar^7$ and $Ar^{11}$ is in ortho-position to the *-position;

X and Y cannot be H and/or $C_1$ to $C_7$ alkyl at the same time;

Q and Y may be substituted with one or more substituents selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

a to k are independently 0 or 1, provided that $2 \leq a+b+c+d+e+f+g+h+i+k \leq 5$;

$Ar^2$ to $Ar^{11}$ are independently selected from the group consisting of substituted or unsubstituted $C_6$ to $C_{12}$ aryl and $C_4$ to $C_{10}$ heterorayl, wherein the one or more substituents, if present in one or more of the groups $Ar^2$ to $Ar^{11}$, are independently selected from the group consisting of $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F and CN;

neither Formula (IV) nor Formula (VII) comprises condensed aromatic rings; and a compound having the following formula is excluded

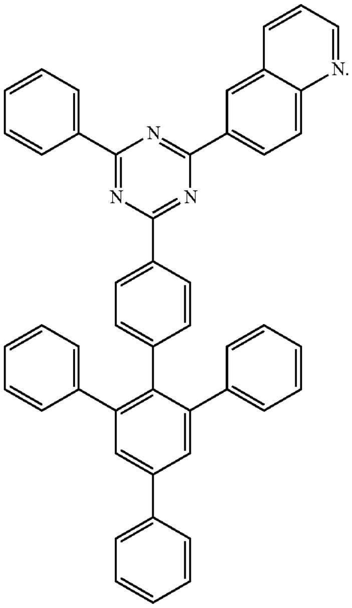 [SMILES: c1ccc(-c2cc(-c3ccccc3)c(-c3ccc(-c4nc(-c5ccccc5)nc(-c5ccc6ncccc6c5)n4)cc3)c(-c3ccccc3)c2)cc1]
Particularly preferred compound of Formula (I) are the following compounds 1 to 74.
1
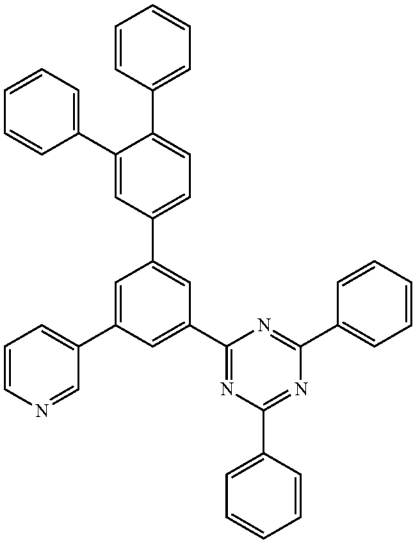
-continued
2
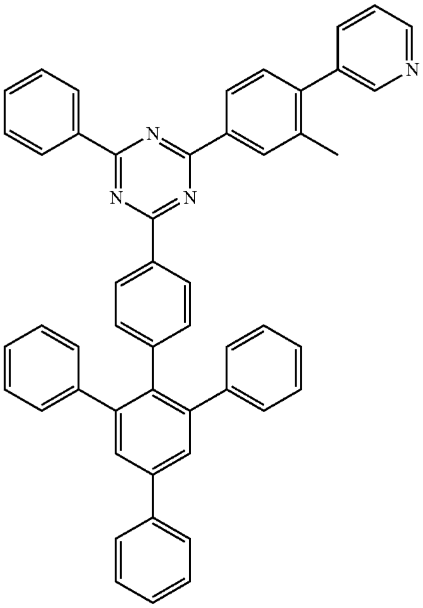
3
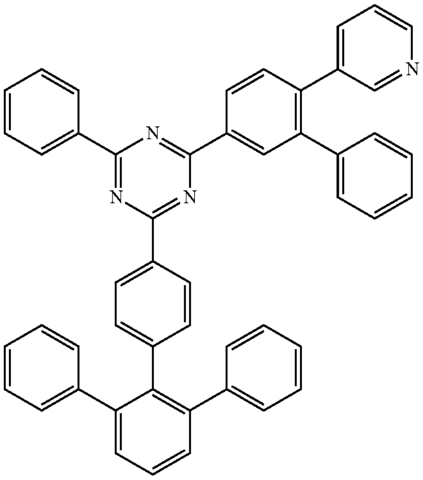

4
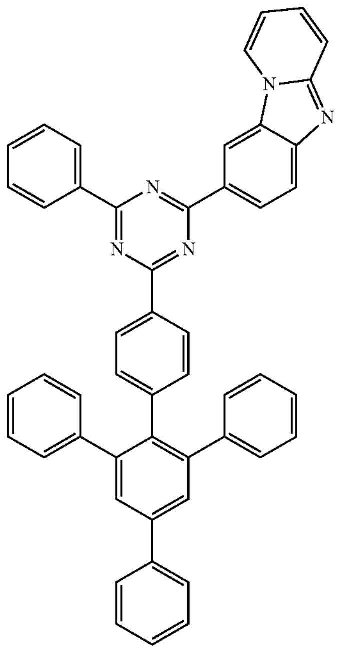
5
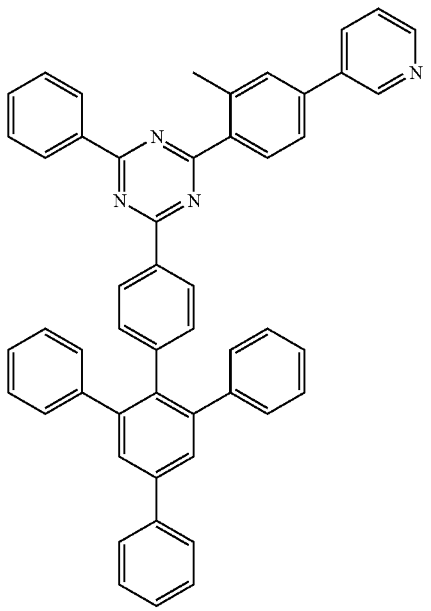
6
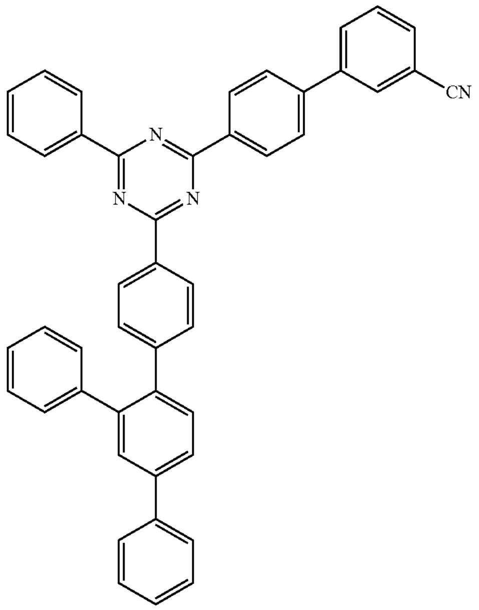
7
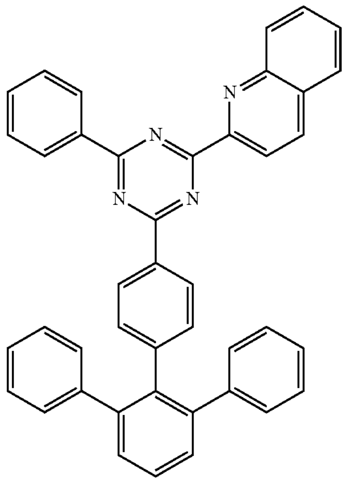
8
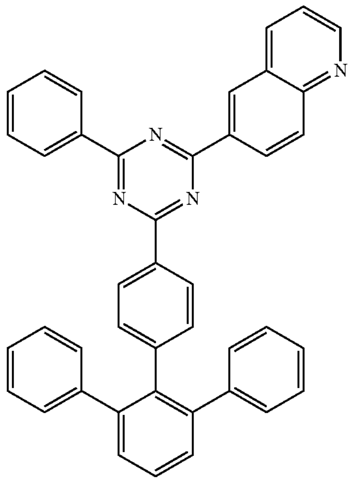

-continued
9
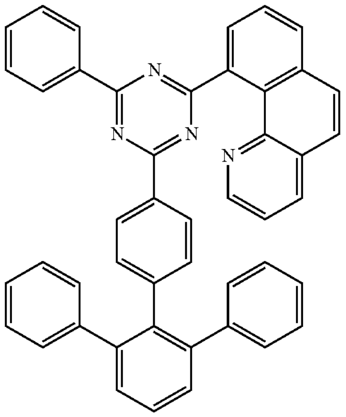
10
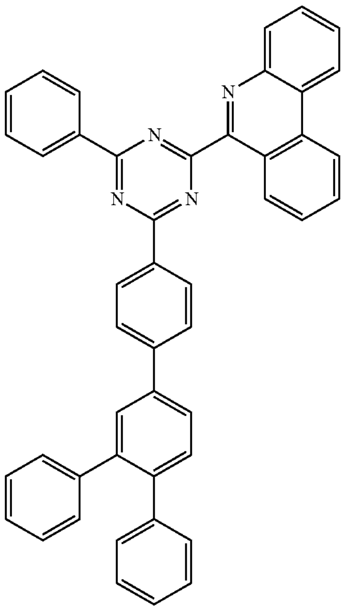
11
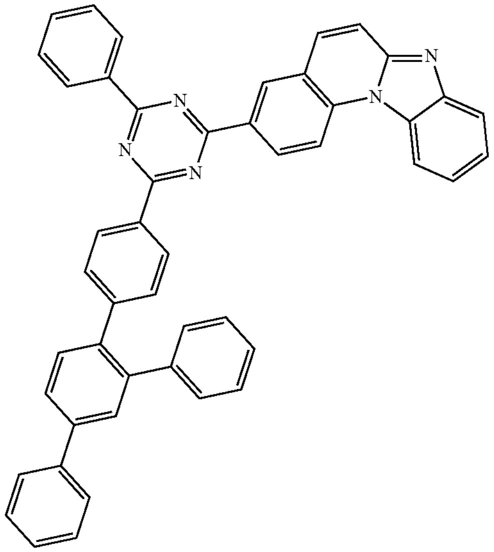
-continued
12
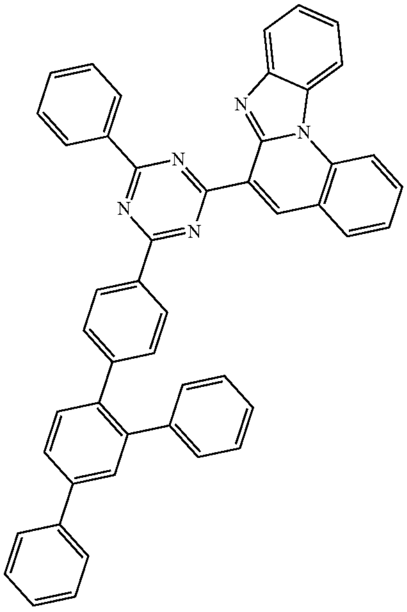
13
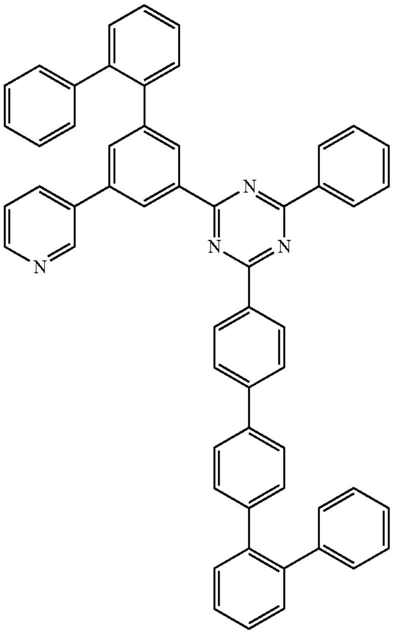

-continued
14
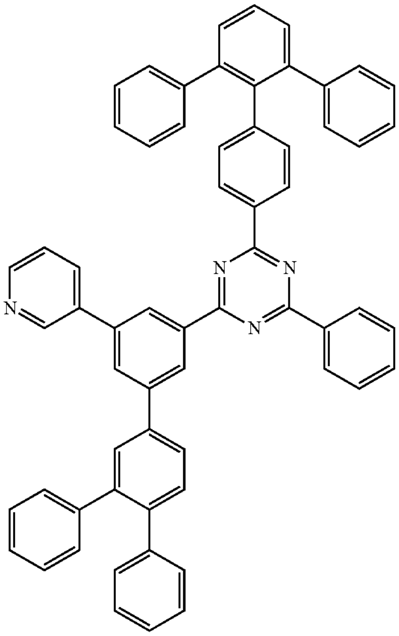
15
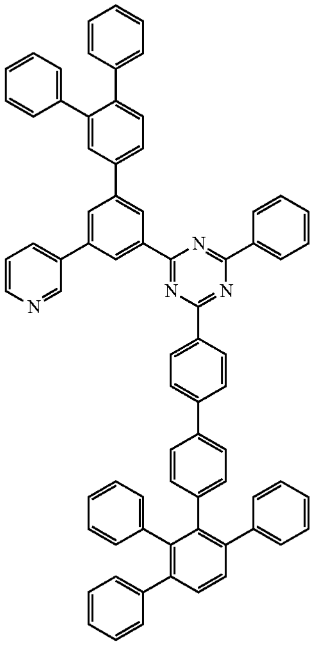
-continued
16
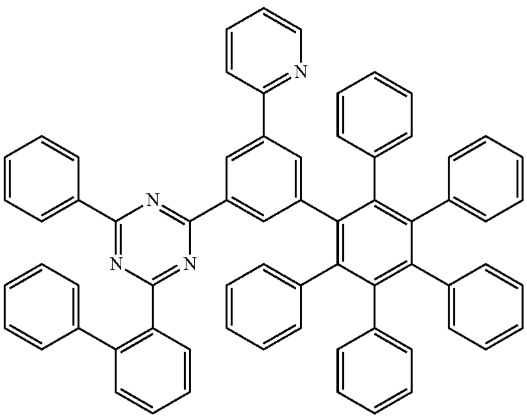
17
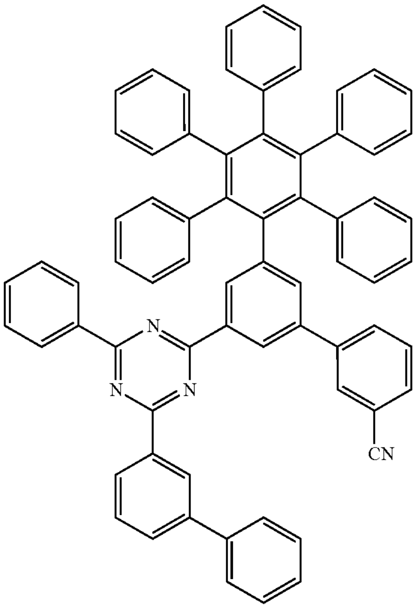
18
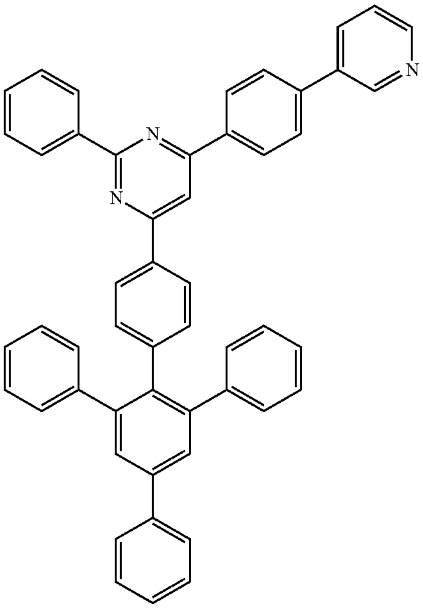

-continued
19
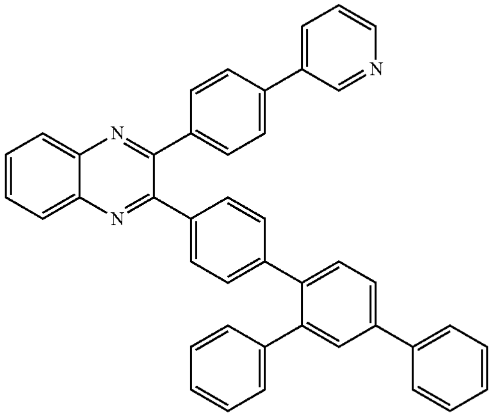
20
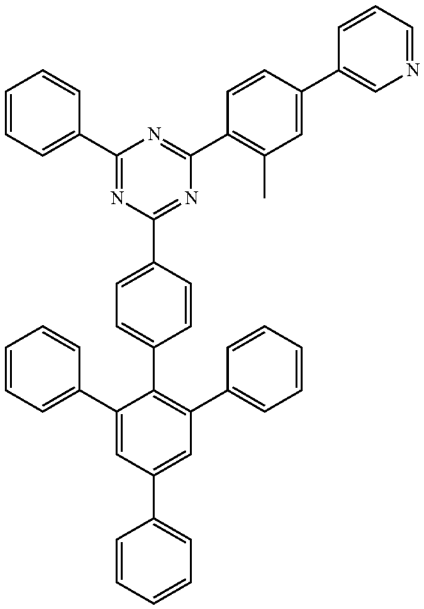
21
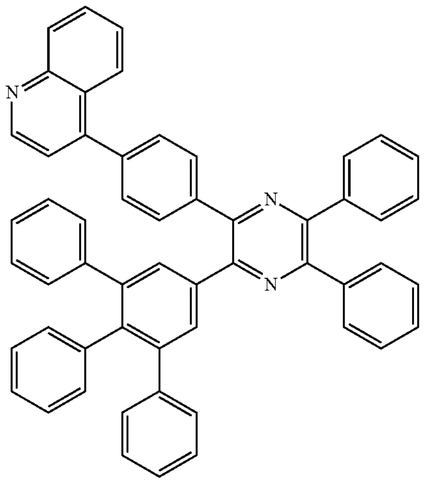
-continued
22
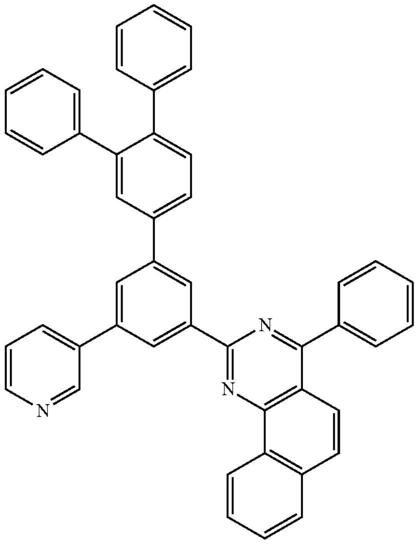
23
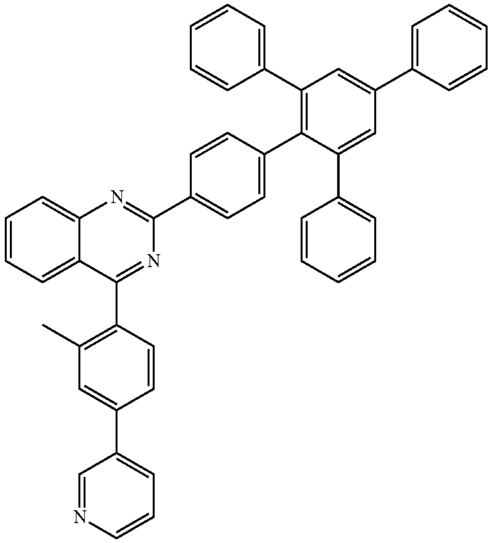
24
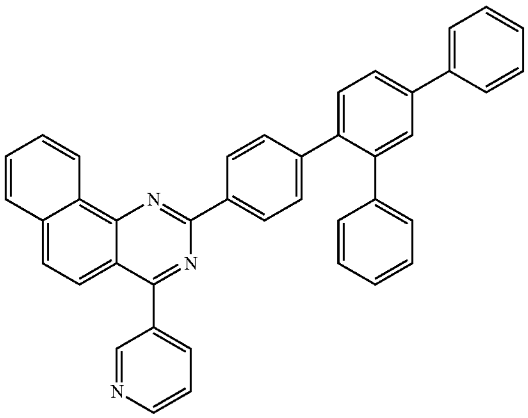

-continued
25
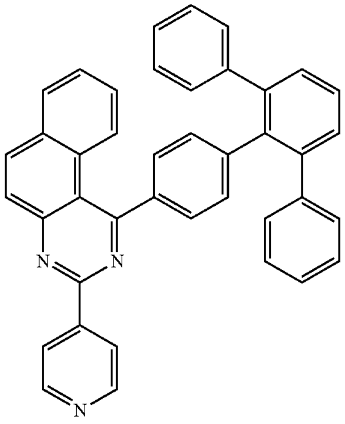
26
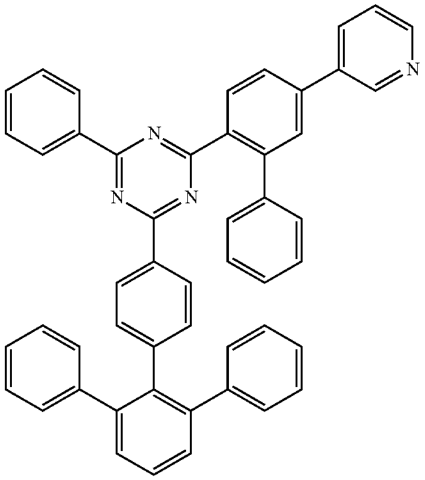
27
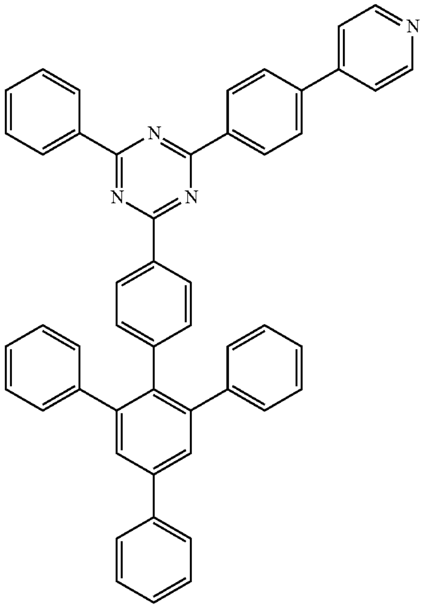
-continued
28
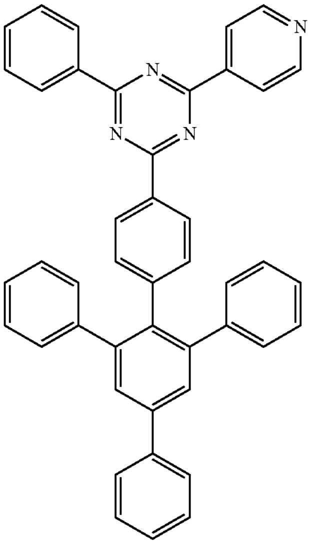
29
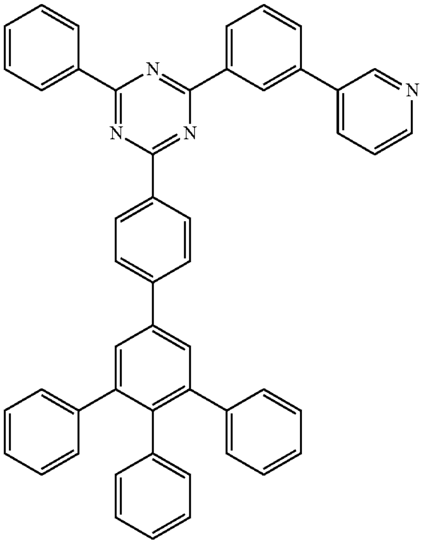
30
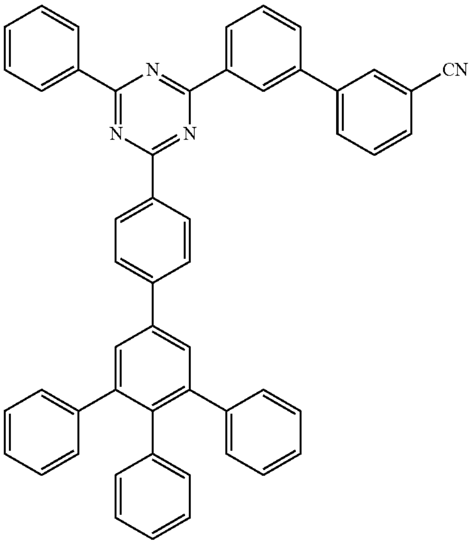

-continued
31
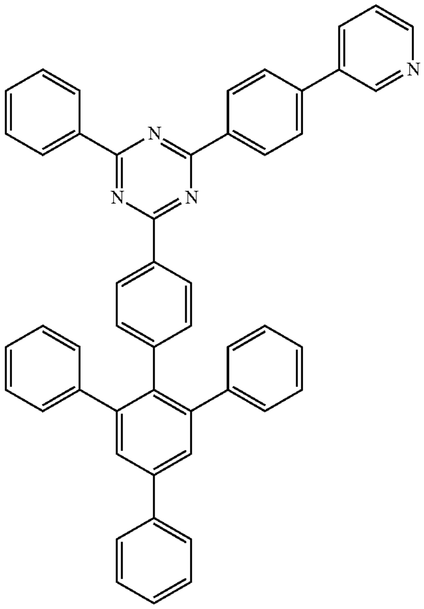
32
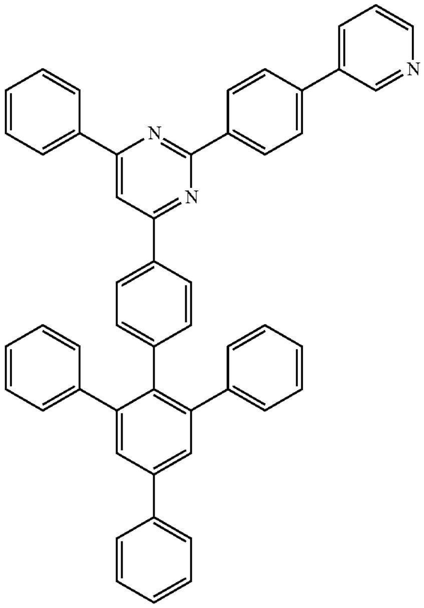
-continued
33
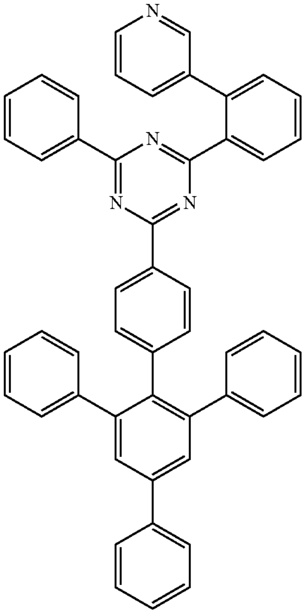
34
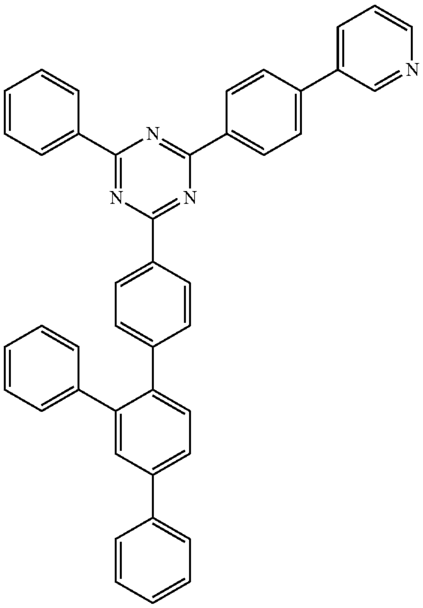

-continued
35
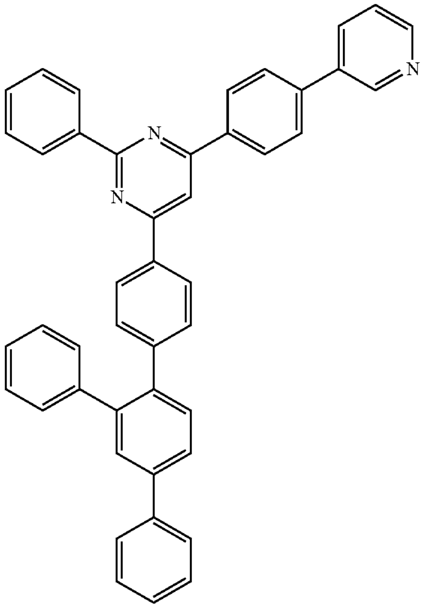
36
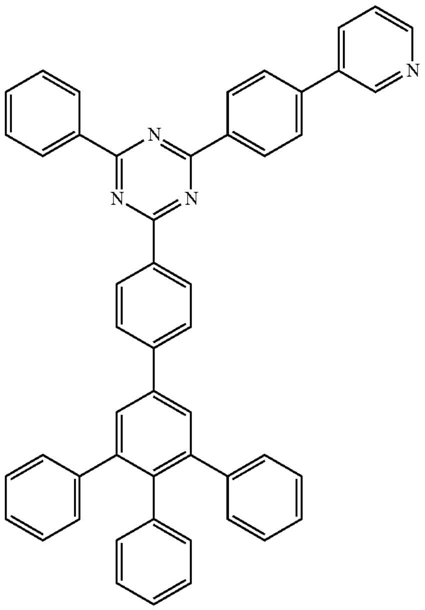
-continued
37
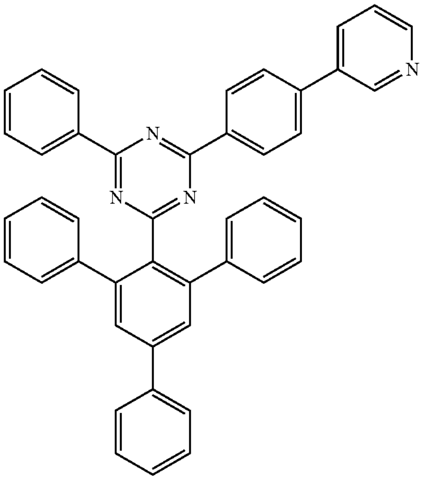
38
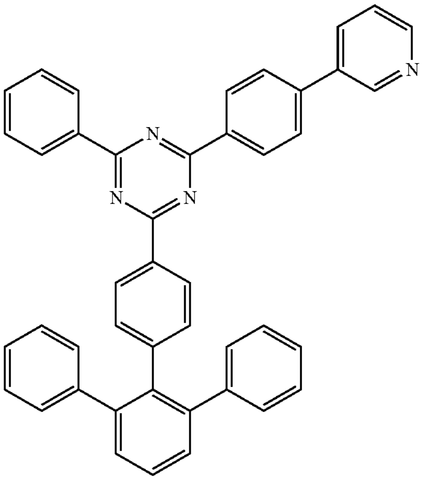
39
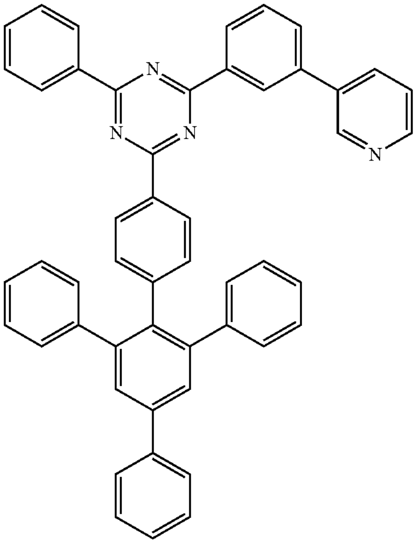

-continued
40
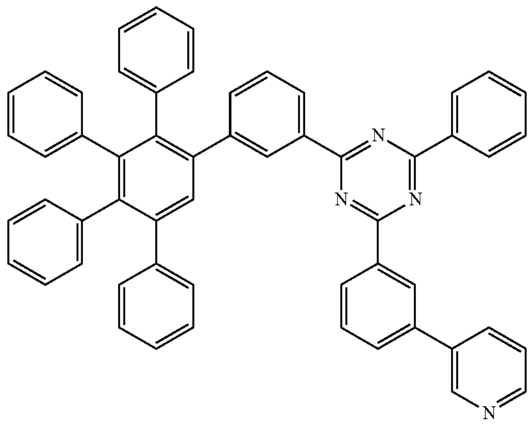
41
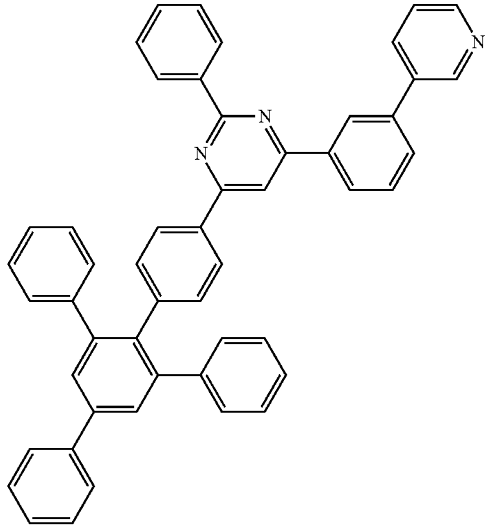
42
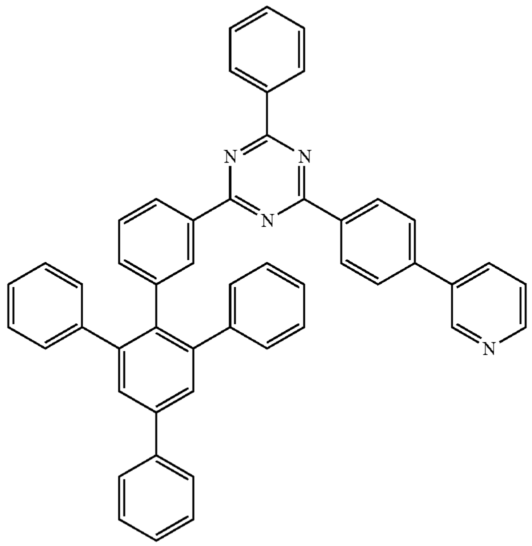
-continued
43
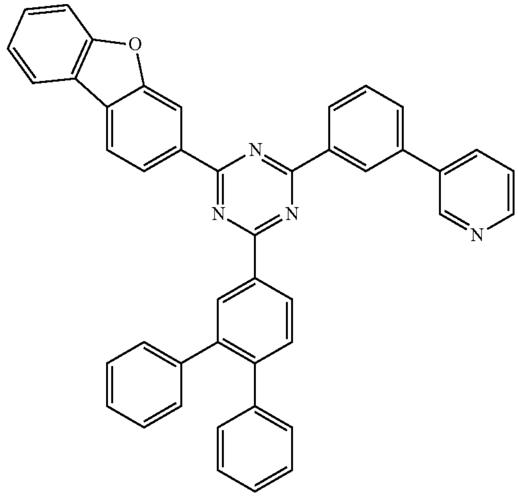
44
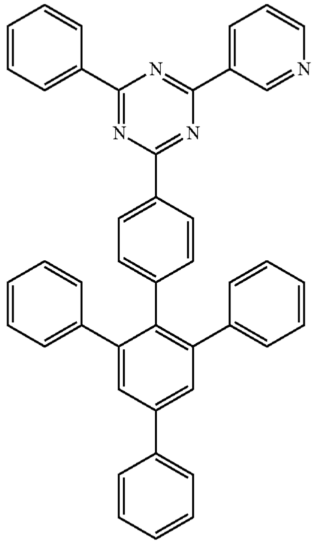
45
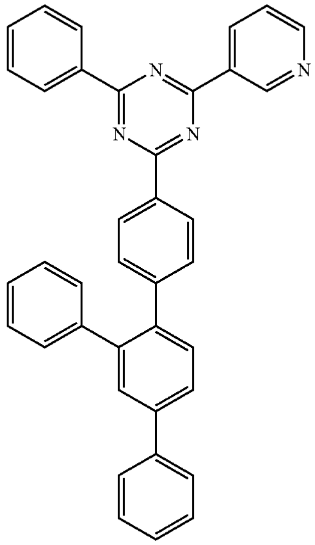

-continued
46
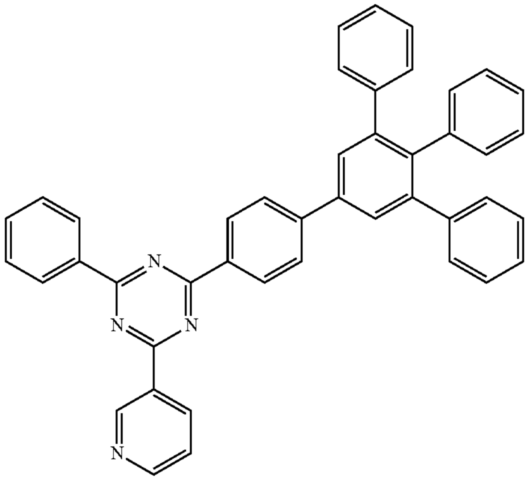
47
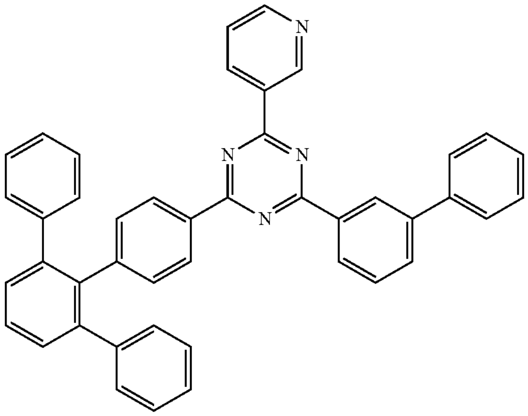
48
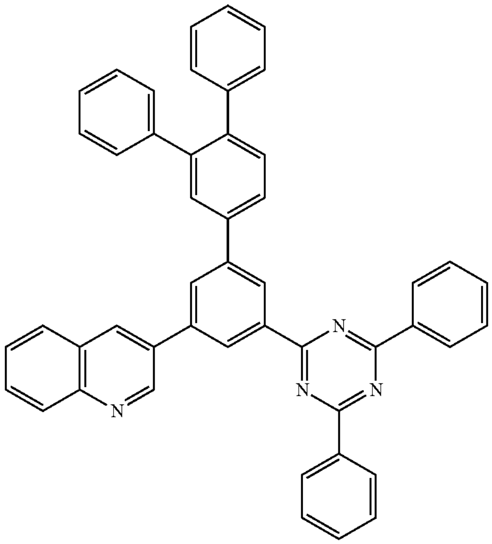
-continued
49
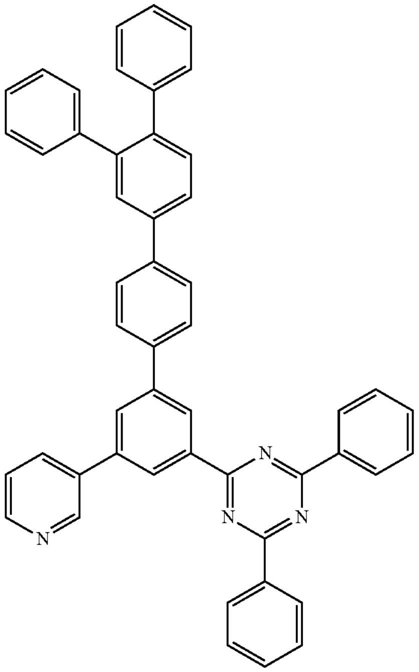
50
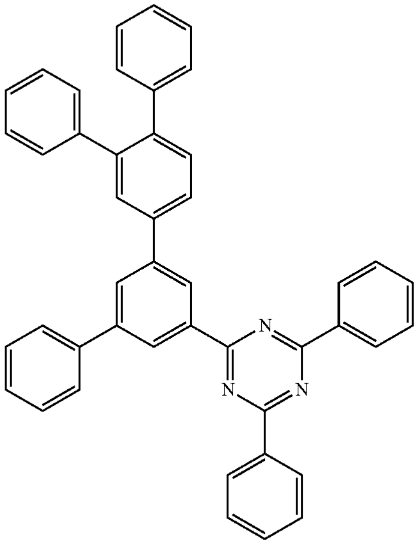

-continued
51
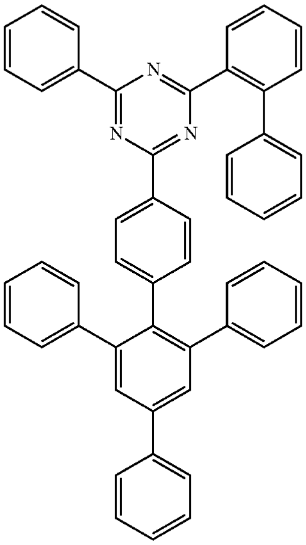
52
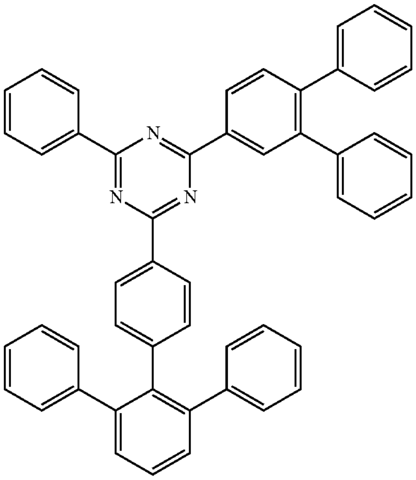
53
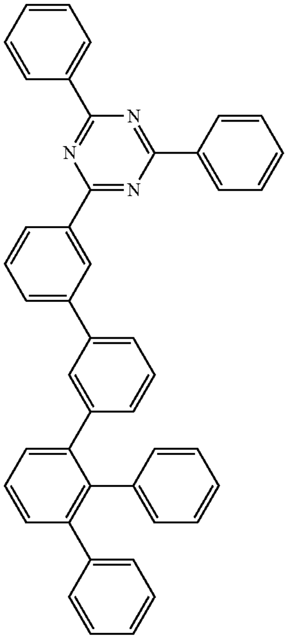
-continued
54
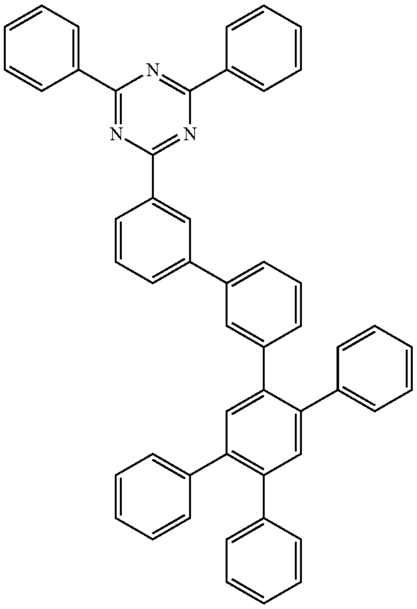
55
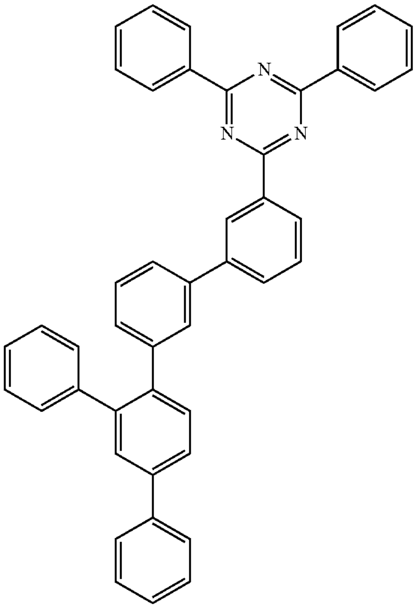

-continued
56
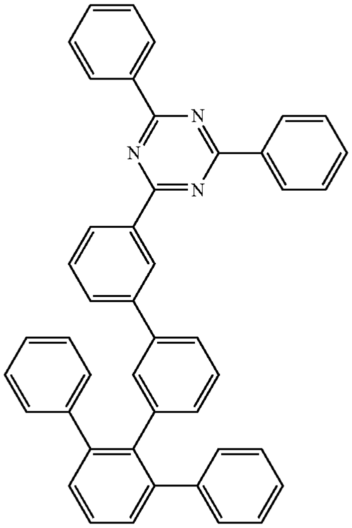
57
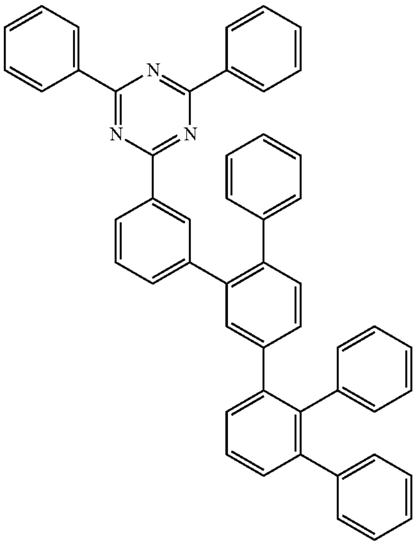
58
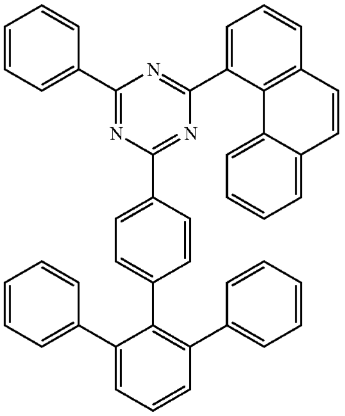
-continued
59
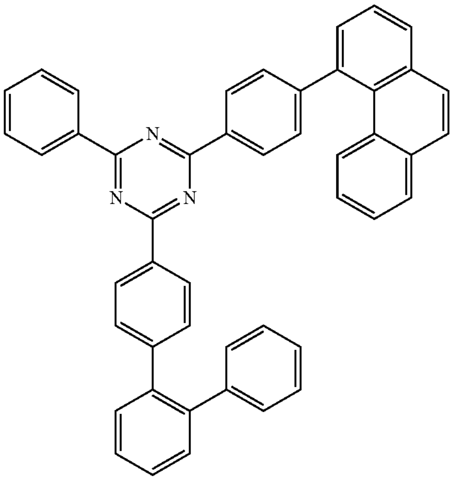
60
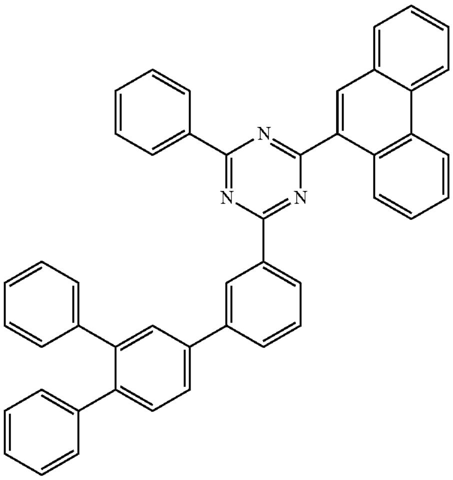
61
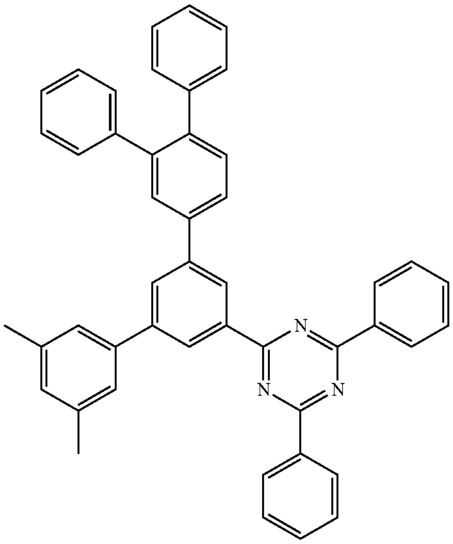

-continued
62
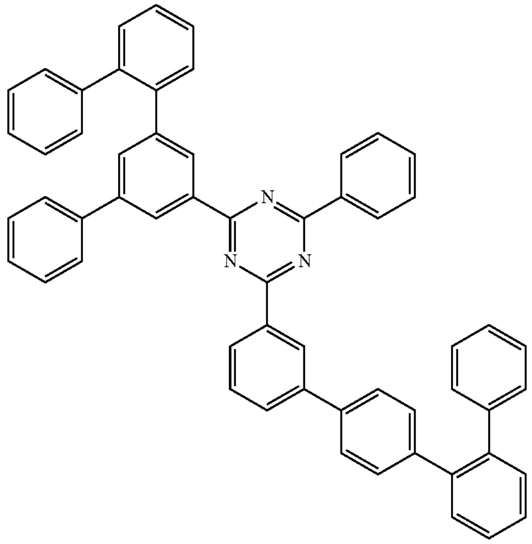
63
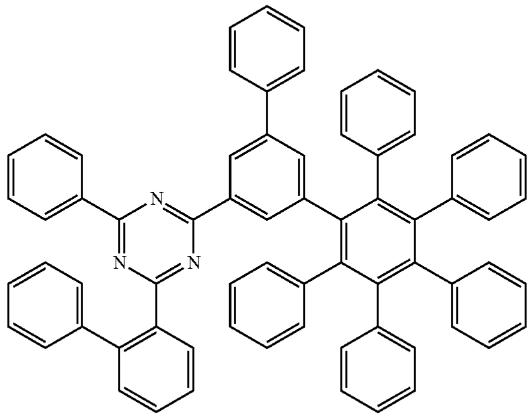
64
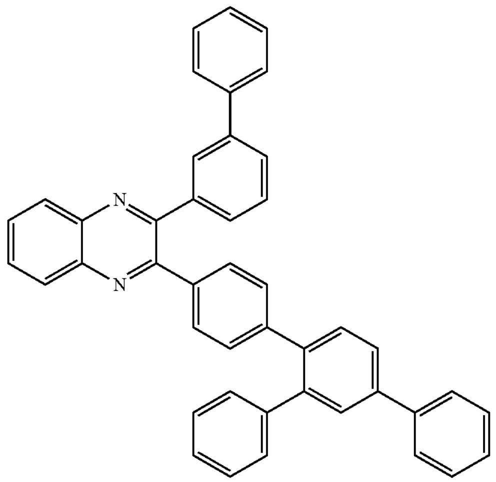
-continued
65
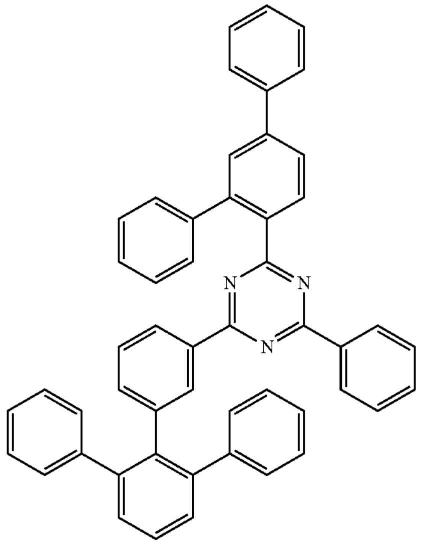
66
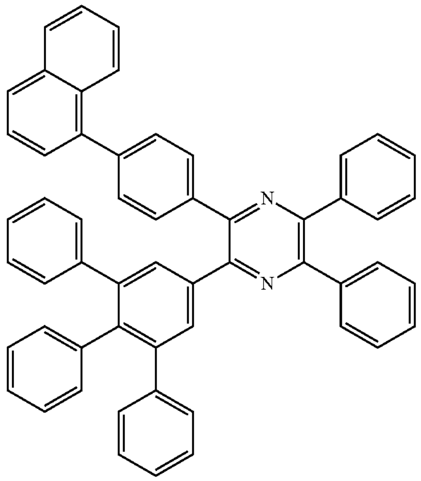
67
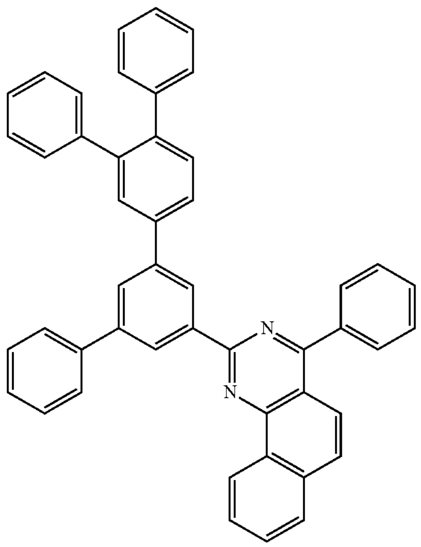

-continued
68
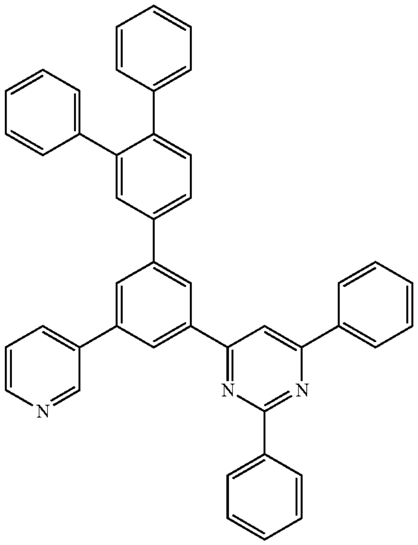
69
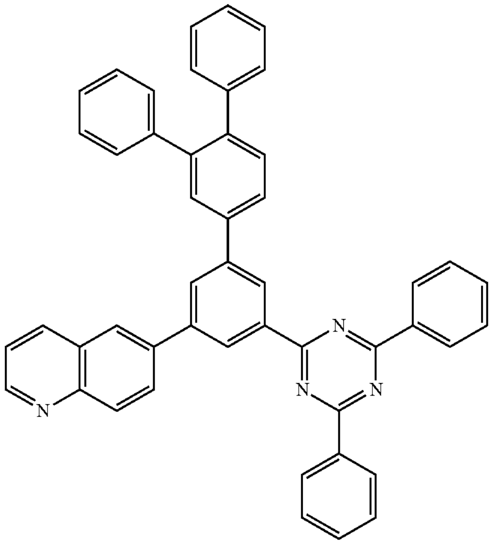
70
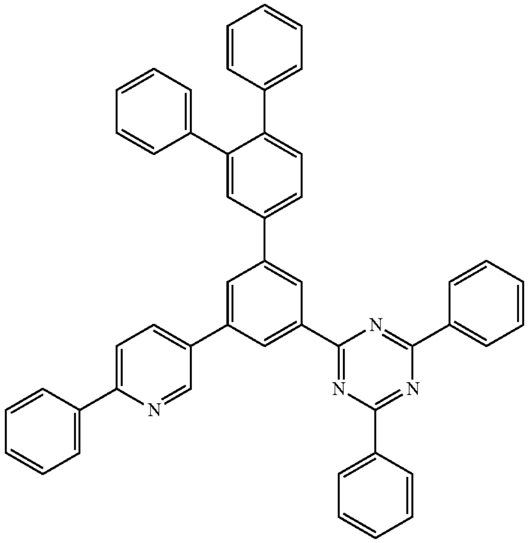
-continued
71
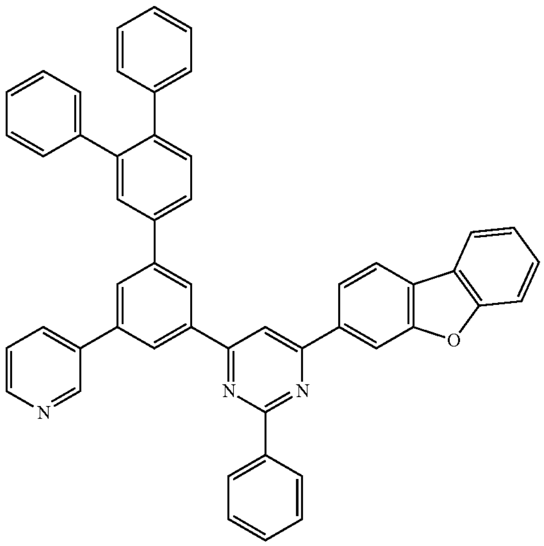
72
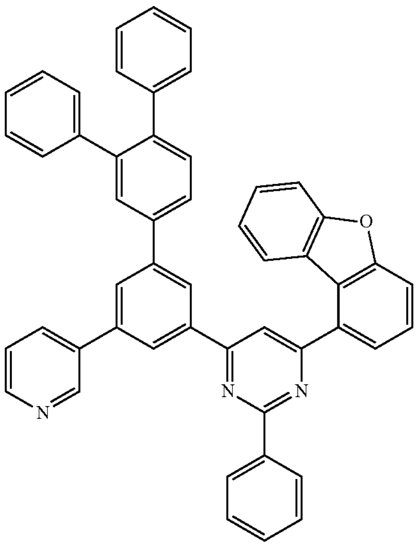
73
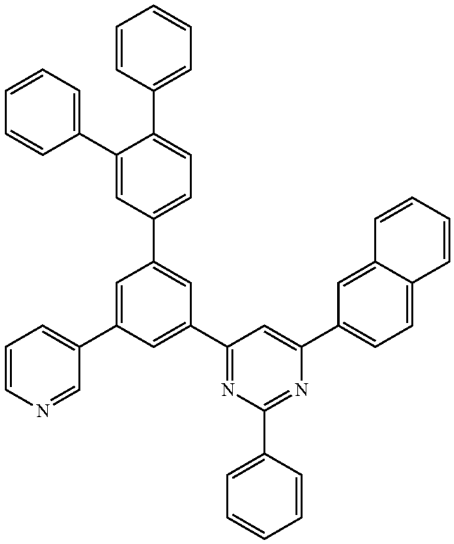

-continued

74

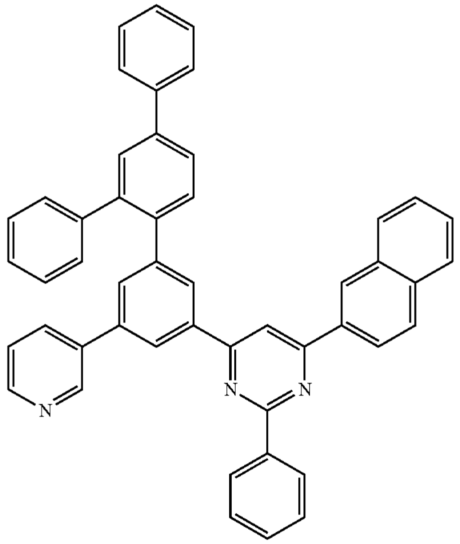

The object is further achieved by an organic semiconducting layer comprising the compound of Formula (I) as defined herein. It may be provided that is the organic semiconducting layer consists of the compound of Formula (I). In one embodiment, the organic semiconducting layer does not contain a dopant or an additive. In an alternative embodiment, it may be provided that the organic semiconducting layer contains a dopant or an additive. The organic semiconducting layer may further comprise at least one second component.

The organic semiconducting layer comprising the compound of Formula (I) as defined herein may further comprise (as a second component) a metal, alternatively an alkali metal, a metal salt alternatively an alkaline earth metal salt and/or rare earth metal salt, or an organic alkali metal complex, alternatively an alkali metal complex, alternatively LiF, LiCl, LiBr, LiI, LiQ or a metal borate.

The organic semiconducting layer may be non-emissive.

The object is further achieved by an organic electronic device comprising the organic semiconducting layer as defined herein.

The organic electronic device may further comprise a first electrode and a second electrode and the organic semiconducting layer may be arranged between the first electrode and the second electrode.

The organic electronic device may further comprise an auxiliary electron transport layer and the organic semiconducting layer is in direct contact with the auxiliary electron transport layer.

The organic electronic device may further comprise an emission layer and the organic semiconducting layer may be in direct contact with the emission layer.

The organic electronic device may further comprise an electron transport layer and the organic semiconducting layer may be in direct contact with the electron transport layer.

The organic electronic device may further comprise a cathode and the organic semiconducting layer may be a direct contact with the cathode.

The organic electronic device may comprise to mission layers and the organic semiconducting layer may be arranged between the two emission layers.

The organic semiconducting layer may be a charge generation layer.

The organic semiconducting layer may be comprised in a p-n-junction.

The organic semiconducting layer may be an electron transport layer and the electron transport layer may comprise comprises one or more additives. The additive may be an n-type dopant.

The organic semiconducting layer may be an electron transport layer and the electron transport layer may consist of a compound of Formula (1). In this case, the organic semiconducting layer may be the hole blocking layer (HBL).

The organic electronic device may further comprise an anode, a cathode and at least one emission layer, wherein the organic semiconducting layer comprising the compound of Formula (I) is arranged between the at least one emission layer and the cathode.

Alternatively, the organic semiconducting layer comprising the compound of Formula (I) may be arranged between an auxiliary electron transport layer and the cathode. The auxiliary electron transport layer may also be described as hole blocking layer.

Alternatively, the organic semiconducting layer comprising the compound of Formula (I) may be arranged between a first and a second emission layer.

The organic electronic device may be an organic light emitting device.

The object is further achieved by a display device comprising the organic electronic device as defined herein.

Finally, the object is achieved by a lighting device comprising the organic electronic device as defined herein.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide (SnO2), aluminum zinc oxide (AlZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL may comprise or consist of p-type dopant and the p-type dopant may be selected from tetrafluoro-tetracyanoquinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl)acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N'-Bis(naphthalen-1-yl)-N,N'-bis(phenyl)-benzidine) doped with F4TCNQ. α-NPD doped with 2,2'-(perfluoronaphthalen-2,6-diylidene) dimalononitrile. The p-type dopant concentrations can be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL. Compounds that can be suitably used are disclosed for example in Yasuhiko Shirota and Hiroshi Kageyama, Chem. Rev. 2007, 107, 953-1010 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nim, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm. A preferred thickness of the HTL may be 170 nm to 200 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 m.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from triarylamine compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer does not comprise the compound of Formula (I).

The emission layer (EML) may be formed of a combination of a host and an emitter dopant. Example of the host are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine(TCTA), 1,3,5-tris(N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzothiazolate)zinc (Zn(BTZ)2).

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4,4'-bis(4-diphenyl amiostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above.

The HBL may also be named auxiliary ETL or a-ETL.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with one embodiment of the invention, the electron transport layer may be the inventive organic semiconducting layer comprising the inventive compound represented by the general Formula (I) as defined herein.

According to various embodiments the OLED may comprise an electron transport layer or an electron transport layer stack comprising at least a first electron transport layer (ETL-1) and at least a second electron transport layer (ETL-2).

By suitably adjusting energy levels of particular layers of the ETL, the injection and transport of the electrons may be controlled, and the holes may be efficiently blocked. Thus, the OLED may have long lifetime, improved performance and stability.

The electron transport layer of the organic electronic device may comprise the compound represented by general Formula (I) as defined above as the organic electron transport matrix (ETM) material. The electron transport layer may comprise, besides or instead of the compound represented by the general Formula (I), further ETM materials known in the art. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined below.

Further, the electron transport layer may comprise one or more additives. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another embodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, Li2O, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL if present. The cathode electrode may be formed of a metal, an alloy, an electrically conductive compound, or a mixture thereof.

The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 mn to about 50 nm, the cathode electrode may be transparent or semitransparent even if formed from a metal or metal alloy.

It is to be understood that the cathode electrode is not part of an electron injection layer or the electron transport layer.

Charge Generation Layer/Hole Generating Layer

The charge generation layer (CGL) may comprise a p-type and an n-type layer. An interlayer may be arranged between the p-type layer and the n-type layer.

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers are used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, FeF3, and SbCl5. Also, the host can be one selected from a group consisting of N,N'-di(naphthalen-1-yl)-N,N-diphenylbenzidine (NPB), N,N'-diphenyl-N,N'-bis(3-methylphenyl)-1,1-biphenyl-4,4'-diamine (TPD) and N,N',N'-tetranaphthylbenzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, an organic semiconducting layer comprising a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I), an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacent arranged to an anode electrode, the anode electrode is adjacent arranged to a first hole injection layer, the first hole injection layer is adjacent arranged to a first hole transport layer, the first hole transport layer is adjacent arranged to a first electron blocking layer, the first electron blocking layer is adjacent arranged to a first emission layer, the first emission layer is adjacent arranged to a first-electron transport layer, the first electron transport layer is adjacent arranged to an n-type charge generation layer, the n-type charge generation layer is adjacent arranged to a hole generating layer, the hole generating layer is adjacent arranged to a second hole transport layer, the second hole transport layer is adjacent arranged to a second electron blocking layer, the second electron blocking layer is adjacent arranged to a second emission layer, between the second emission layer and the cathode electrode an optional electron transport layer and/or an optional injection layer are arranged.

The organic semiconducting layer according to the invention may be the electron transport layer, first electron transport layer, n-type charge generation layer and/or second electron transport layer.

For example, the OLED according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound according to Formula (I).

An organic electronic device according to one embodiment may include a substrate, an anode layer, an organic semiconducting layer comprising a compound of Formula (I) and a cathode layer.

An organic electronic device according to one embodiment comprises at least one organic semiconducting layer comprising at least one compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:

at least one deposition source, preferably two deposition sources and more preferred at least three deposition sources.

The methods for deposition that can be suitable comprise:

deposition via vacuum thermal evaporation;

deposition via solution processing, preferably the processing is selected from spin-coating, printing, casting; and/or slot-die coating.

According to various embodiments of the present invention, there is provided a method using:

a first deposition source to release the compound of Formula (I) according to the invention, and a second deposition source to release the metal, a metal salt or an alkali or alkaline earth metal complex; alternatively an organic alkali or alkaline earth metal complex; alternatively 8-hydroxyquinolinolato lithium or alkali borate;

the method comprising the steps of forming the organic semiconducting layer; whereby for an organic light-emitting diode (OLED):

the organic semiconducting layer is formed by releasing the compound of Formula (I) according to the invention from the first deposition source and a metal, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein on a substrate a first anode electrode is formed, on the first anode electrode an emission layer is formed, on the emission layer an electron transport layer stack is formed, optionally a hole blocking layer is formed on the emission layer and an organic semiconducting layer is formed, and finally a cathode electrode is formed, optional a hole injection layer, a hole transport layer, and a hole blocking layer, formed in that order between the first anode electrode and the emission layer, optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:

anode, hole injection layer, first hole transport layer, second hole transport layer, emission layer, optional hole blocking layer, organic semiconducting layer comprising a compound of Formula (I) according to the invention, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

(XX)

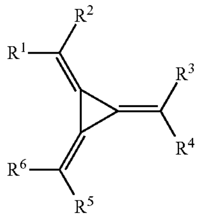

-continued (XXIa)

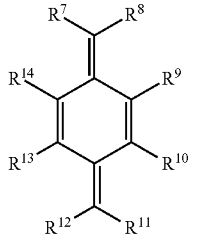

(XXIb)

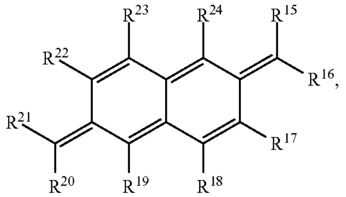

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^9$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

Details and Definitions of the Invention

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

As used herein if not explicitly mentioned else, the asterisk symbol "*" represents a binding position at which the moiety labelled accordingly is bond to another moiety.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthrene, tetracene etc.. Further encompassed are biphenyl and oligo- or polyphenyls, such as terphenyl, phenyl-substituted biphenyl, phenyl-substituted terphenyl (such as tetraphenyl benzole groups) etc.. "Arylene" respectively "heteroarylene", refers to groups to which two further moieties are attached. In the present specification, the term "aryl group" or "arylene group" may refer to a group comprising at least one hydrocarbon aromatic moiety, and all the elements of the hydrocarbon aromatic moiety may have p-orbitals which form conjugation, for example a phenyl group, a napthyl group, an anthracenyl group, a phenanthrenyl group, a pyrinyl group, a fluorenyl group and the like. Further encompoassed are spiro compounds in which two aromatic moieties are connected with each other via a spiro-atom, such as 9,9'-spirobi [9H-fluorene]yl. The aryl or arylene group may include a monocyclic or fused ring polycyclic (i.e., links sharing adjacent pairs of carbon atoms) functional group.

The term "heteroaryl" as used herein refers to aryl groups in which at least one carbon atom is substituted with a heteroatom. The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably, a heteroarylene ring may comprise at least 1 to 3 heteroatoms individually selected from N, S and/or O. Just as in case of "aryl"/"arylene", the term "heteroaryl" comprises, for example, spiro compounds in which two aromatic moieties are connected with each other, such as spiro[fluorene-9,9'-xanthene]. Further exemplary heteroaryl groups are diazine, triazine, dibenzofurane, dibenzothiofurane, acridine, benzoacridine, dibenzoacridine etc.

The term "alkenyl" as used herein refers to a group $-CR^1{=}CR^2R^3$ comprising a carbon-carbon double bond.

The term "perhalogenated" as used herein refers to a hydrocarbyl group wherein all of the hydrogen atoms of the hydrocarbyl group are replaced by halogen (F, Cl, Br, I) atoms.

The term "alkoxy" as used herein refers to a structural fragment of the Formula —OR with R being hydrocarbyl, preferably alkyl or cycloalkyl.

The term "thioalkyl" as used herein refers to a structural fragment of the Formula —SR with R being hydrocarbyl, preferably alkyl or cycloalkyl.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" as used herewith shall encompass pyridine, quinoline, benzoquinoline, quinazoline, benzoquinazoline, pyrimidine, pyrazine, triazine, benzimidazole, benzothiazole, benzo[4,5]thieno[3,2-d]pyrimidine, carbazole, xanthene, phenoxazine, benzoacridine, dibenzoacridine and the like.

In the present specification, the term single bond refers to a direct bond.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer. With respect to the inventive organic semiconducting layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term, "about" the claims include equivalents to the quantities.

It should be noted that, as used in this specification and the appended claims, the singular forms, "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound of Formula (I) is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at 10 milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
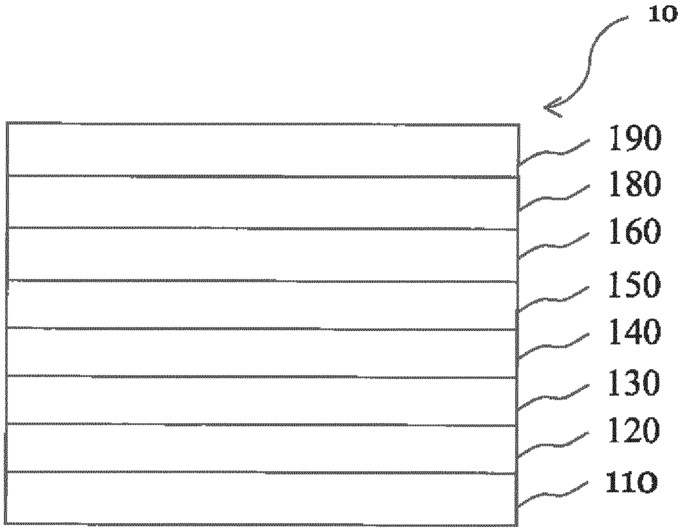
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
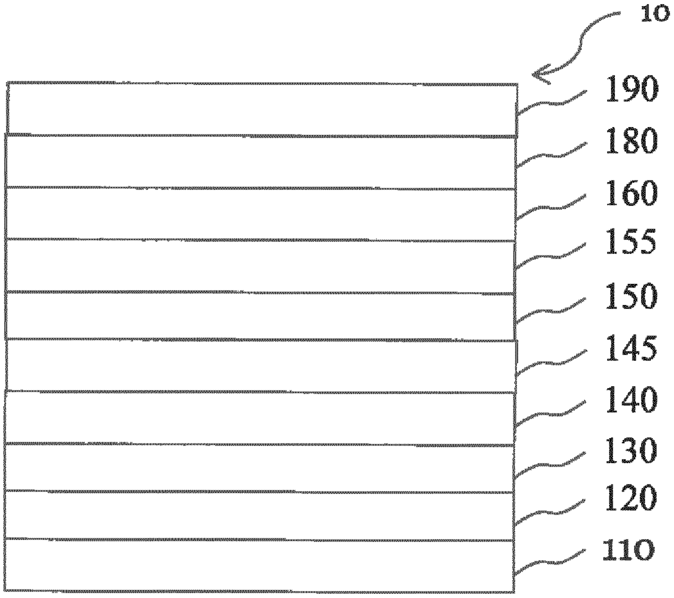
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) may be an ETL.

Figure 3:
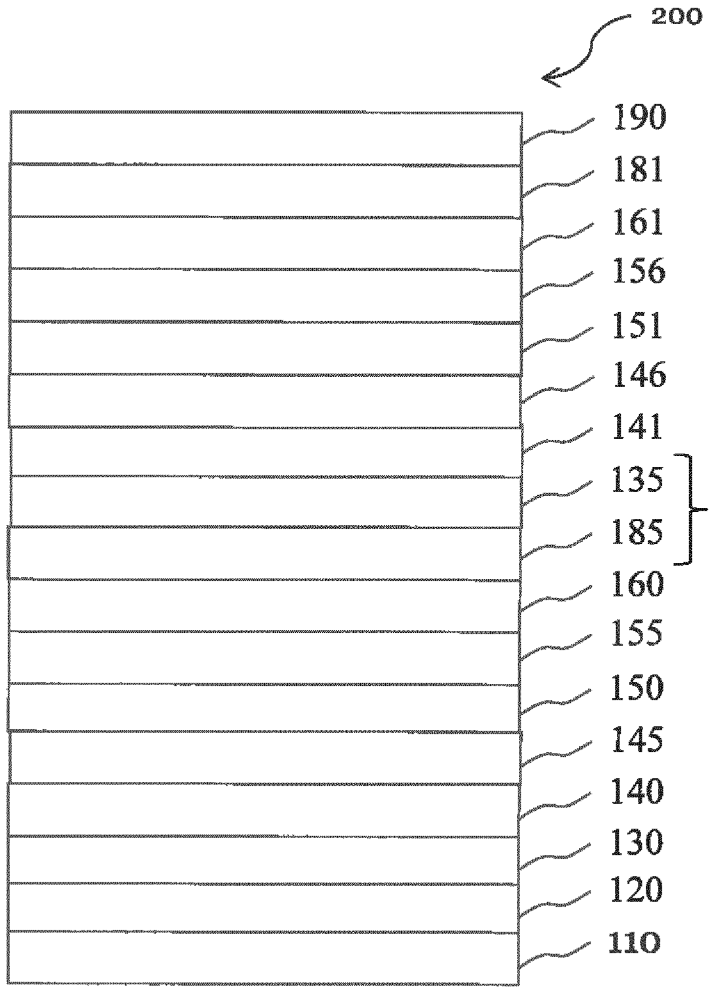
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) may be the first ETL, n-type CGL and/or second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Data

Melting Point

The melting point (mp) is determined as peak temperatures from the DSC curves of the above TGA-DSC measurement or from separate DSC measurements (Mettler Toledo DSC822e, heating of samples from room temperature to completeness of melting with heating rate 10 K/min under a stream of pure nitrogen. Sample amounts of 4 to 6 mg are placed in a 40 μL Mettler Toledo aluminum pan with lid, a<1 mm hole is pierced into the lid).

Glass Transition Temperature

The glass transition temperature (Tg) is measured under nitrogen and using a heating rate of 10 K per min in a Mettler Toledo DSC 822e differential scanning calorimeter as described in DIN EN ISO 11357, published in March 2010.

Rate Onset Temperature

The rate onset temperature (TRO) is determined by loading 100 mg compound into a VTE source. As VTE source a point source for organic materials may be used as supplied by Kurt J. Lesker Company (www.lesker.com) or CreaPhys GmbH (http://www.creaphys.com). The VTE source is heated at a constant rate of 15 K/min at a pressure of less than 10-5 mbar and the temperature inside the source measured with a thermocouple. Evaporation of the compound is detected with a QCM detector which detects deposition of the compound on the quartz crystal of the detector. The deposition rate on the quartz crystal is measured in Angstrom per second. To determine the rate onset temperature, the deposition rate is plotted against the VTE source temperature. The rate onset is the temperature at which noticeable deposition on the QCM detector occurs. For accurate results, the VTE source is heated and cooled three time and only results from the second and third run are used to determine the rate onset temperature.

To achieve good control over the evaporation rate of an organic compound, the rate onset temperature may be in the range of 200 to 255° C. If the rate onset temperature is below 200° C. the evaporation may be too rapid and therefore difficult to control. If the rate onset temperature is above 255° C. the evaporation rate may be too low which may result in low tact time and decomposition of the organic compound in VTE source may occur due to prolonged exposure to elevated temperatures.

The rate onset temperature is an indirect measure of the volatility of a compound. The higher the rate onset temperature the lower is the volatility of a compound.

Reduction Potential

The reduction potential is determined by cyclic voltammetry with potenioststic device Metrohm PGSTAT30 and software Metrohm Autolab GPES at room temperature. The redox potentials given at particular compounds were measured in an argon de-aerated, dry 0.1M THF solution of the tested substance, under argon atmosphere, with 0.1M tetrabutylammonium hexafluorophosphate supporting electrolyte, between platinum working electrodes and with an Ag/AgCl pseudo-standard electrode (Metrohm Silver rod electrode), consisting of a silver wire covered by silver chloride and immersed directly in the measured solution, with the scan rate 100 mV/s. The first run was done in the broadest range of the potential set on the working electrodes, and the range was then adjusted within subsequent runs appropriately. The final three runs were done with the addition of ferrocene (in 0.1M concentration) as the standard. The average of potentials corresponding to cathodic and anodic peak of the studied compound, after subtraction of the average of cathodic and anodic potentials observed for the standard $Fc^+/Fc$ redox couple, afforded finally the values reported above. All studied compounds as well as the reported comparative compounds showed well-defined reversible electrochemical behaviour.

Dipole Moment

The dipole moment $|\vec{\mu}|$ of a molecule containing N atoms is given by:

$$\vec{\mu} = \sum_{i}^{N} q_i \vec{r_i}$$

$$|\vec{\mu}| = \sqrt{\mu_x^2 + \mu_y^2 + \mu_z^2}$$

where $q_i$ and $\vec{r}_i$ are the partial charge and position of atom i in the molecule.

The dipole moment is determined by a semi-empirical molecular orbital method.

The geometries of the molecular structures are optimized using the hybrid functional B3LYP with the 6-31G* basis set in the gas phase as implemented in the program package TURBOMOLE V6.5 (TURBOMOLE GmbH, Litzenhardtstrasse 19, 76135 Karlsruhe, Germany). If more than one conformation is viable, the conformation with the lowest total energy is selected to determine the bond lengths of the molecules.

Calculated HOMO and LUMO

The HOMO and LUMO are calculated with the program package TURBOMOLE V6.5 (TURBOMOLE GmbH, Litzenhardtstrasse 19, 76135 Karlsruhe, Germany). The optimized geometries and the HOMO and LUMO energy levels of the molecular structures are determined by applying the hybrid functional B3LYP with a 6-31G* basis set in the gas phase. If more than one conformation is viable, the conformation with the lowest total energy is selected.Measurement of OLED Performance To assess the performance of the OLED devices the current efficiency is measured at 20° C. The current-voltage characteristic is determined using a Keithley 2635 source measure unit, by sourcing a voltage in V and measuring the current in mA flowing through the device under test. The voltage applied to the device is varied in steps of 0.1 V in the range between 0V and 10V. Likewise, the luminance-voltage characteristics and CIE coordinates are determined by measuring the luminance in $cd/m^2$ using an Instrument Systems CAS-140CT array spectrometer (calibrated by Deutsche Akkreditierungsstelle (DAkkS)) for each of the voltage values. The cd/A efficiency at 10 $mA/cm^2$ is determined by interpolating the luminance-voltage and current-voltage characteristics, respectively.

Lifetime LT of the device is measured at ambient conditions (20° C.) and 30 $mA/cm^2$, using a Keithley 2400 sourcemeter, and recorded in hours.

The brightness of the device is measured using a calibrated photo diode. The lifetime LT is defined as the time till the brightness of the device is reduced to 97% of its initial value. The increase in operating voltage OU is used as a measure of the operating voltage stability of the device. This increase is determined during the LT measurement and by subtracting the operating voltage at the start of operation of the device from the operating voltage after 50 hours.

□U=[U(50 h)−U(0 h)]

The smaller the value of DU the better is the operating voltage stability.

Synthesis Procedures

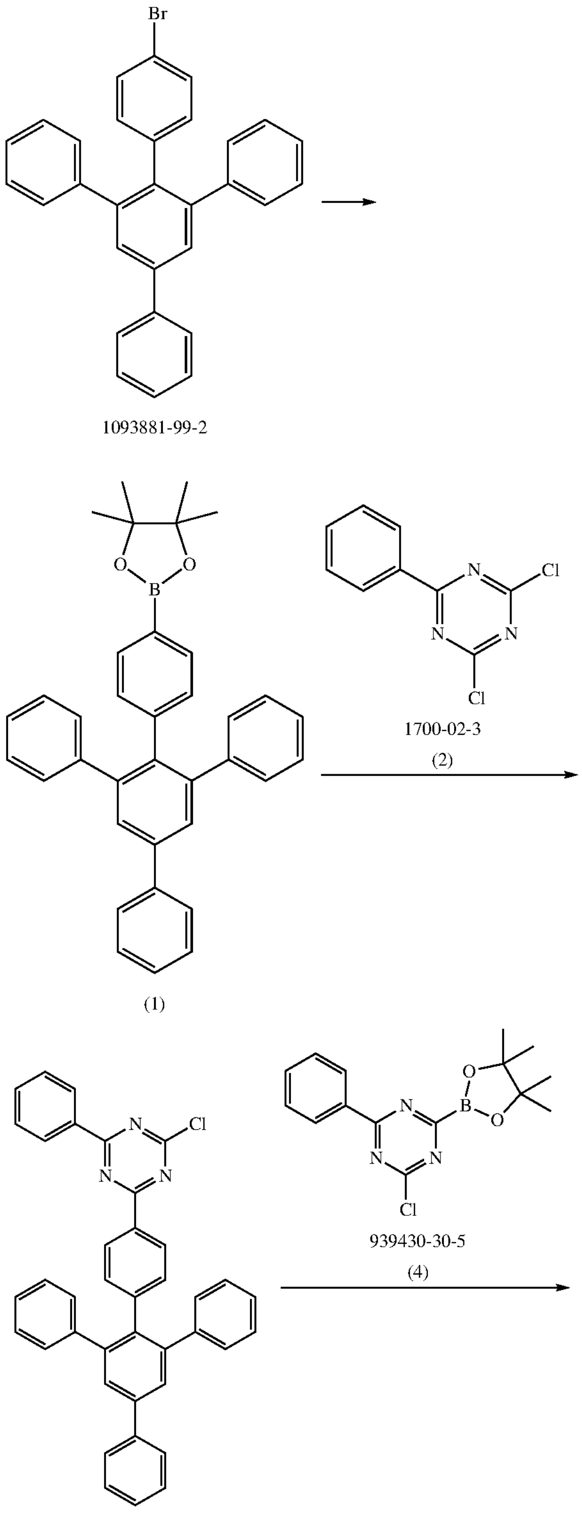

1093881-99-2

1700-02-3

(2)

(1)

939430-30-5

(4)

(3)

-continued

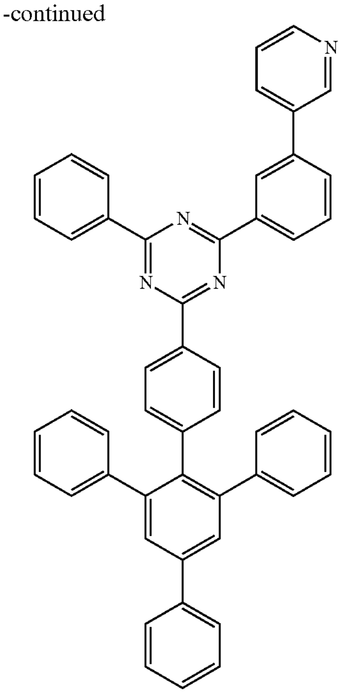

M-1

Compound (1) was synthesized following a standard Suzuki-Miyaura procedure (reference KR2017093023A)

2-chloro-4-(2',6'-diphenyl-[1,1':4',1"-terphenyl]-4-yl)-6-phenyl-1,3,5-triazine (3)

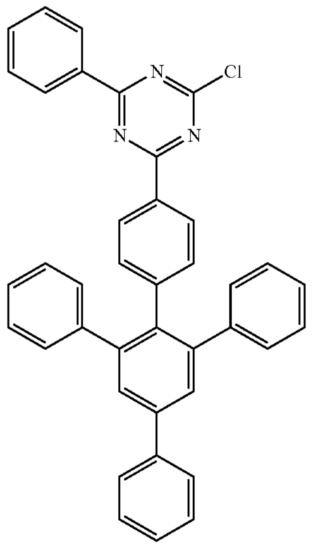 [SMILES: Clc1nc(-c2ccccc2)nc(-c2ccc(-c3c(-c4ccccc4)cc(-c4ccccc4)cc3-c3ccccc3)cc2)n1]

A flask was flushed with nitrogen and charged with 2-(2',6'-diphenyl-[1,1':4',1"-terphenyl]-4-yl)-4,4,5,5-tetramethyl-1,3,2-dioxaborolane (1) (100 g, 196.7 mmol), 2,4-dichloro-6-phenyl-1,3,5-triazine (2) (68.0 g, 295 mmol), Pd(dppf)$Cl_2$ (7.2 g, 9.8 mmol), and $K_2CO_3$ (67.9 g, 491.7 mmol). A mixture of deaerated Toluene/THF/water (1:1:1, 1200 mL) was added and the reaction mixture was heated to 65° C. under a nitrogen atmosphere overnight. Solvent was partially evaporated under reduced pressure and the resulting precipitate was isolated by suction filtration and washed thoroughly with water (600 mL), methanol (20 mL) and hexane (20 mL). The crude product was dissolved in toluene (600 mL) and filtered over a pad of silicagel. After rinsing with additional toluene, solvents were partially removed and the suspension was left stirring overnight. Precipitate was filtered, washed with hexane, recrystallized in toluene two times, and dried under vacuum to yield 36.5 g (32%) of white solid after drying. HPLC: 99%.

2-(2',6'-diphenyl-[1,1':4',1"-terphenyl]-4-yl)-4-phenyl-6-(3-(pyridin-3-yl)phenyl)-1,3,5-triazine (M-1)

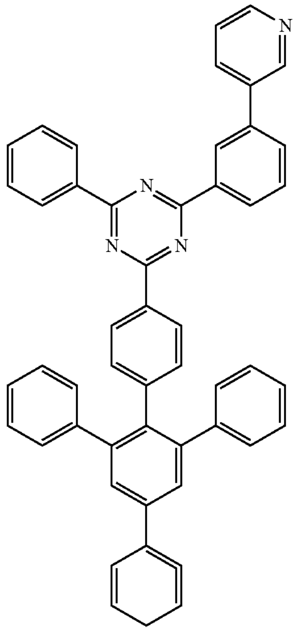 [SMILES: C1=CCC=CC=1c1cc(-c2ccccc2)c(-c2ccc(-c3nc(-c4ccccc4)nc(-c4cccc(-c5cccnc5)c4)n3)cc2)c(-c2ccccc2)c1]

A flask was flushed with nitrogen and charged with 2-chloro-4-(2', 6'-diphenyl-[1,1': 4', 1"-terphenyl]-4-yl)-6-phenyl-1,3,5-triazine (3) (15.5 g, 26.4 mmol), 3-(3-(4,4,5,5-tetramethyl-1,3,2-dioxaborolan-2-yl)phenyl)pyridine (4) (7.4 g, 26.4 mmol), Pd(dppf)$Cl_2$ (0.4 g, 0.5 mmol), and $K_2CO_3$ (7.3 g, 52.8 mmol). A mixture of deaerated THF/water (4:1, 132 mL) was added and the reaction mixture was heated to 75° C. under a nitrogen atmosphere overnight. Solvent was evaporated under reduced pressure and the compound (embedded in silicagel) was purified by silicagel column chromatography, using a gradient eluent (dichloromethane/hexane 1:2 to dichloromethane). Solvent was evaporated under reduced pressure and the resulting solid was triturated in methanol to yield 6.2 g (32%) of white solid after drying. Final purification was achieved by sublimation. HPLC/ESI-MS: 99.97%, m/z=691 ($[M+H]^+$).

-continued

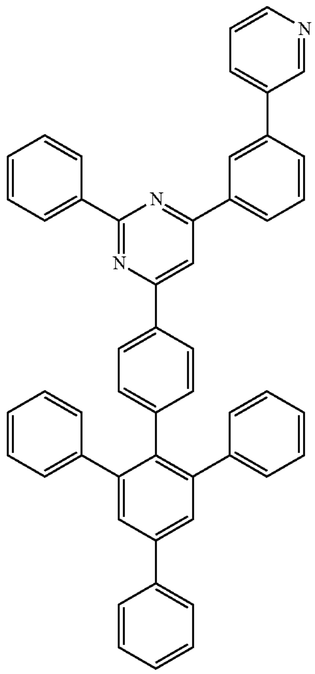

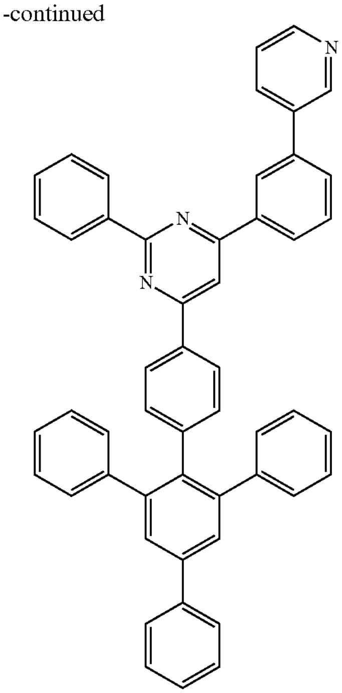

M-2

4-chloro-6-(2',6'-diphenyl-[1,1':4',1"-terphenyl]-4-yl)-2-phenylpyrimidine (6)

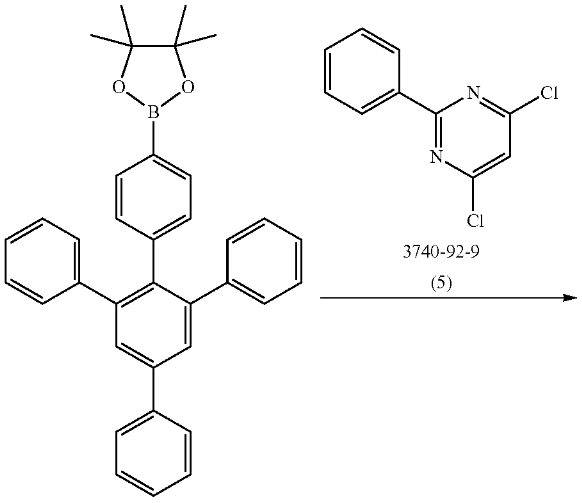

(1)

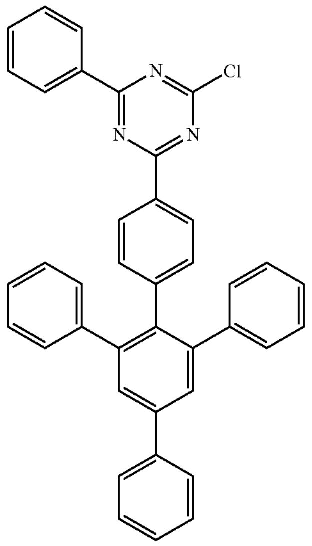 [SMILES: Clc1nc(-c2ccccc2)nc(-c2ccc(-c3c(-c4ccccc4)cc(-c4ccccc4)cc3-c3ccccc3)cc2)n1]

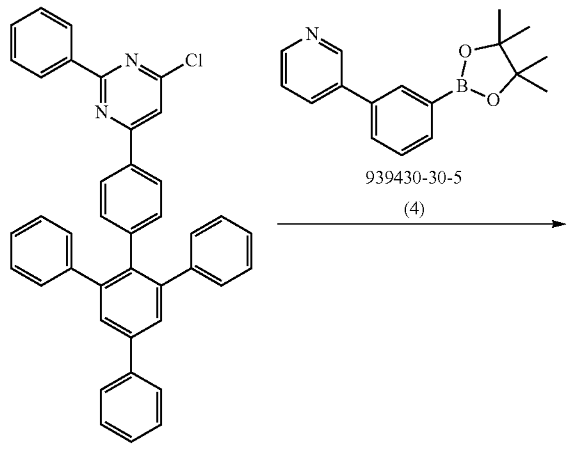

(6)

A flask was flushed with nitrogen and charged with 2-(2',6'-diphenyl-[1,1': 4', 1"-terphenyl]-4-yl)-4,4,5,5-tetramethyl-1,3,2-dioxaborolane (1) (100 g, 196.7 mmol), 4,6-dichloro-2-phenylpyrimidine (5) (66.4 g, 295.0 mmol), $Pd(dppf)Cl_2$ (7.2 g, 9.8 mmol), and $K_2CO_3$ (67.9 g, 491.7 mmol). A mixture of deaerated THF/Toluene/water (1:1:1, 1200 mL) was added and the reaction mixture was heated to 60° C. under a nitrogen atmosphere overnight. After cooling down to room temperature, the resulting precipitate was isolated by suction filtration and washed thoroughly with water (3 L), methanol (2×70 mL) and hexane (2×50 mL). The crude product was then triturated first in Toluene/THF 1:1 (600 mL), and then in toluene (500 mL) to yield 71.2 g (60%) of white solid after drying. HPLC: 99%.

4-(2', 6'-diphenyl-[1,1': 4', 1"-terphenyl]-4-yl)-2-phenyl-6-(3-(pyridin-3-yl)phenyl)pyrimidine (M-2)

A flask was flushed with nitrogen and charged with 4-chloro-6-(2', 6'-diphenyl-[1,1': 4', 1"-terphenyl]-4-yl)-2-phenylpyrimidine (6) (20 g, 35.0 mmol), 3-(3-(4,4,5,5-tetramethyl-1,3,2-dioxaborolan-2-yl)phenyl)pyridine (4) (10.8 g, 38.5 mmol), Pd(PPh3)4 (0.8 g, 0.7 mmol), and $K_2CO_3$ (9.7 g, 70.0 mmol). A mixture of dioxane/water (280:35 mL) was added and the reaction mixture was heated to 75° C. under a nitrogen atmosphere over two days. After cooling down to room temperature, the resulting precipitate was isolated by suction filtration and washed thoroughly with water (600 mL), methanol (20 mL) and hexane (20 mL). The crude product was dissolved in dichloromethane (1.6 L) and filtered over a pad of silicagel. After rinsing with additional dichloromethane (2 L) and dichloromethane: methanol (100: 5), solvents were partially removed under reduced pressure and hexane (300 mL) was added to induce precipitation. Precipitate was filtered, washed with hexane and dried under vacuum to yield 16 g (66%) of white solid after drying. Final purification was achieved by sublimation. HPLC/ESI-MS: 100%, m/z=690 ($[M+H]^+$).

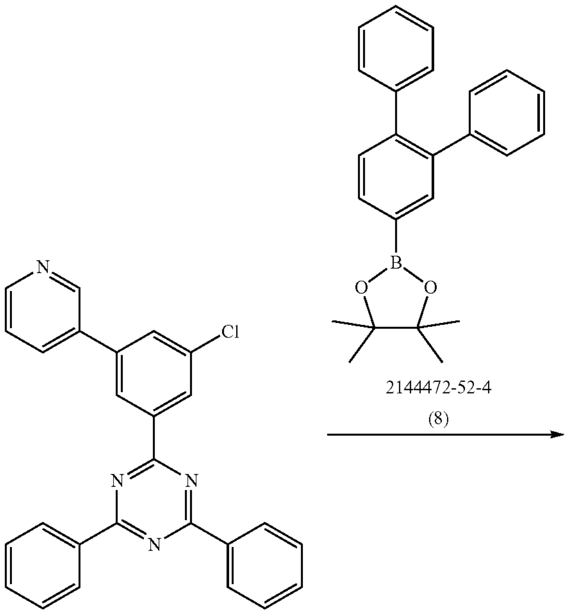

1643448-24-1
(7)

-continued

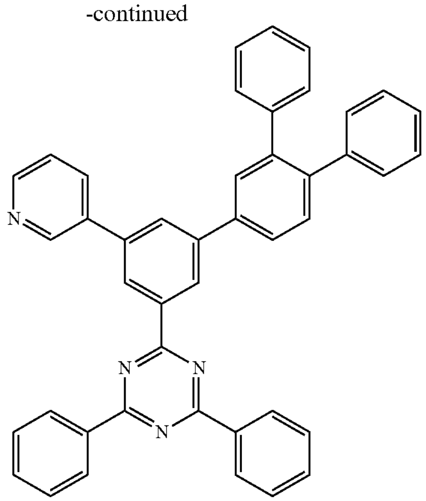

M-3

2,4-diphenyl-6-(4'-phenyl-5-(pyridin-3-yl)-[1,1': 3', 1"-terphenyl]-3-yl)-1,3,5-triazine (M3)

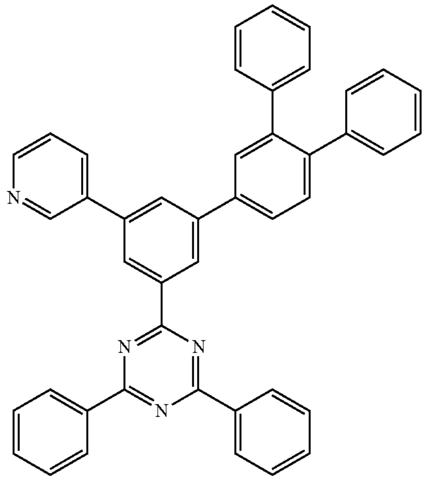 [SMILES: c1ccc(-c2nc(-c3ccccc3)nc(-c3cc(-c4cccnc4)cc(-c4ccc(-c5ccccc5)c(-c5ccccc5)c4)c3)n2)cc1]

A flask was flushed with nitrogen and charged with 2-(3-chloro-5-(pyridin-3-yl)phenyl)-4,6-diphenyl-1,3,5-triazine (7) (5.0 g, 11.9 mmol), 2-([1,1':2',1"-terphenyl]-4'-yl)-4,4,5,5-tetramethyl-1,3,2-dioxaborolane (8) (5.5 g, 15.4 mmol), chloro(crotyl)(2-dicyclohexylphosphino-2',6'-dimethoxybiphenyl)palladium(II) (0.14 g, 0.2 mmol), and $K_3PO_4$ (5.0 g, 23.8 mmol). A mixture of dioxane/water (4:1, 68 mL) was added and the reaction mixture was heated to 45° C. under a nitrogen atmosphere overnight. After cooling down to room temperature, the resulting precipitate was isolated by suction filtration and washed thoroughly with water (400 mL), methanol (20 mL) and hexane (20 mL). The crude product was dissolved in dichloromethane: hexane (1:1, 800 mL) and filtered over a pad of silicagel. After rinsing with additional dichloromethane/hexane (1:1, 800 mL) and dichloromethane (500 mL), solvents were partially removed under reduced pressure and hexane (300 mL) was added to induce precipitation. Precipitate was filtered, washed with hexane and dried under vacuum to yield 5.8 g (80%) of white solid after drying. Final purification was achieved by sublimation. HPLC/ESI-MS: 99.9%, m/z=615 ($[M+H]^+$).

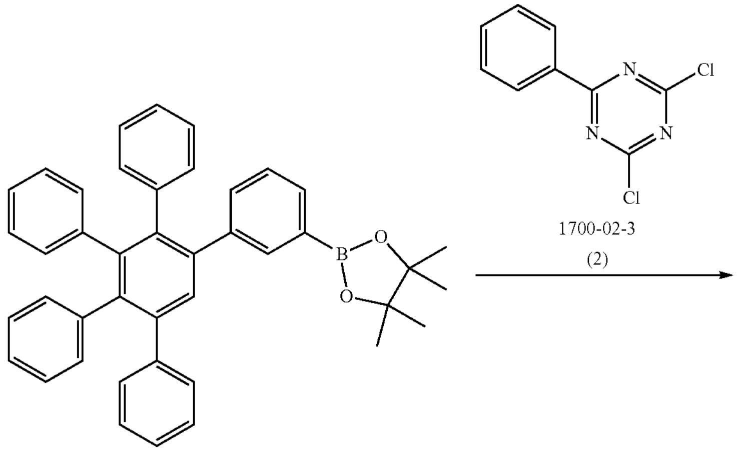
1700-02-3
(2)
872118-08-6
(9)
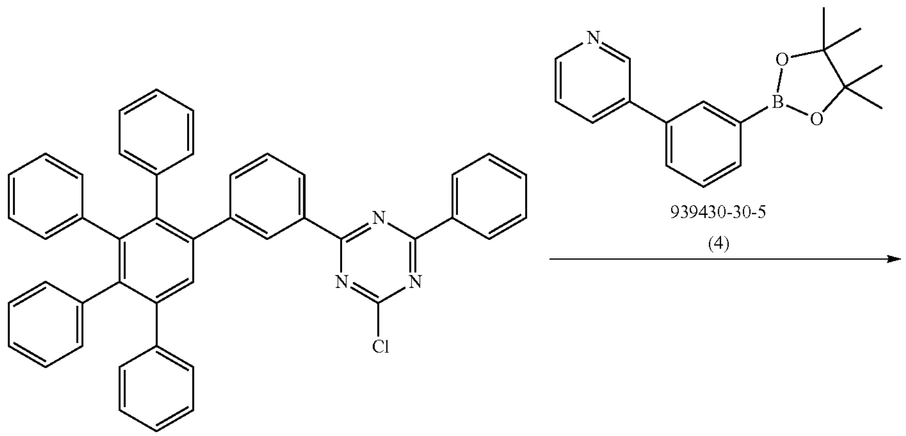
939430-30-5
(4)
(10)
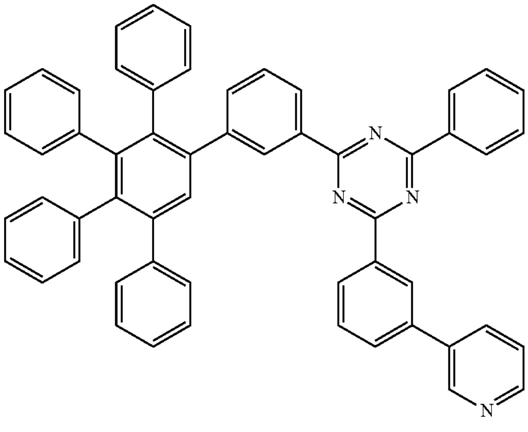
M-4

2-chloro-4-phenyl-6-(3', 4', 5'-triphenyl-[1,1': 2', 1"-terphenyl]-3-yl)-1,3,5-triazine (10)

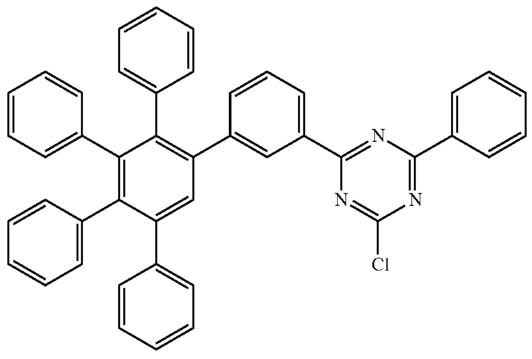 [SMILES: Clc1nc(-c2ccccc2)nc(-c2cccc(-c3cc(-c4ccccc4)c(-c4ccccc4)c(-c4ccccc4)c3-c3ccccc3)c2)n1]

A flask was flushed with nitrogen and charged with 4,4,5,5-tetramethyl-2-(3',4',5'-triphenyl-[1,1':2',1"-terphenyl]-3-yl)-1,3,2-dioxaborolane (9) (60.0 g, 102.6 mmol), 2,4-dichloro-6-phenyl-1,3,5-triazine (2) (27.3 g, 120.8 mmol), Pd(dppf)$Cl_2$ (4.4 g, 6.0 mmol), and $K_2CO_3$ (41.7 g, 301.9 mmol). A mixture of Toluene/THF/water (1:1:1, 1050 mL) was added and the reaction mixture was heated to 65° C. under a nitrogen atmosphere overnight. After cooling down to room temperature, the aqueous phase was decanted, and the organic phase was washed with water (2×250 mL), dried over $Mg_2SO_4$. Drying agent was filtered off and solvents were removed under reduced pressure. Residue was dissolved in dichloromethane and filtered over a silicagel pad. After rinsing with hexane/ethylacetate (20:1), solvents were removed under reduced pressure to yield 24 g (36%) of solid after drying. HPLC: 99%.

2-phenyl-4-(3-(pyridin-3-yl)phenyl)-6-(3',4',5'-triphenyl-[1,1':2',1'''-terphenyl]-3-yl)-1,3,5-triazine (M-4)

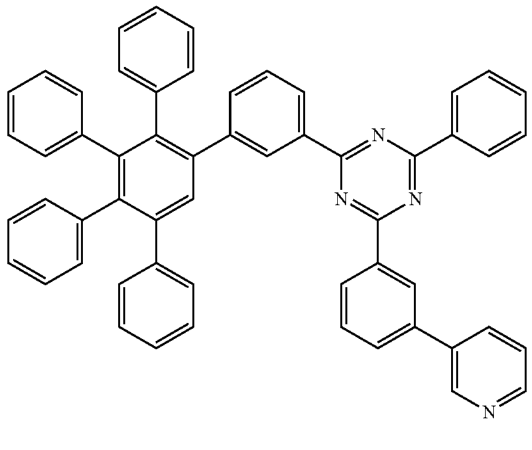 [SMILES: c1ccc(-c2nc(-c3cccc(-c4cccnc4)c3)nc(-c3cccc(-c4cc(-c5ccccc5)c(-c5ccccc5)c(-c5ccccc5)c4-c4ccccc4)c3)n2)cc1]

A flask was flushed with nitrogen and charged with 2-chloro-4-phenyl-6-(3',4',5'-triphenyl-[1,1':2',1"-terphenyl]-3-yl)-1,3,5-triazine (10) (11.9 g, 18.4 mmol), 3-(3-(4,4,5,5-tetramethyl-1,3,2-dioxaborolan-2-yl)phenyl)pyridine (4), (5.7 g, 20.2 mmol), Pd(dppf)$Cl_2$ (0.3 g, 0.37 mmol), and $K_2CO_3$ (5.1 g, 36.8 mmol). A mixture of THF/water (4:1, 125 mL) was added and the reaction mixture was heated to 75° C. under a nitrogen atmosphere for two hours. After cooling down to room temperature, solvents were removed under reduced pressure. The crude reaction mixture was dissolved in dichloromethane (400 mL), washed with water (3×300 mL), dried over $Mg_2SO_4$ and directly filtered over a fluorisil pad. After rinsing with additional dichloromethane/methanol (100:2, 2.5 L), solvents were partially removed under reduced pressure and isopropanol (400 mL) was added to induce precipitation. Precipitate was filtered and washed with isopropanol. Solid was dissolved in toluene (40 mL), methanol (200 mL) was added to induce precipitation. Precipitate was filtered, washed with methanol and dried under vacuum to yield 4.4 g (32%) of light pink solid after drying. Final purification was achieved by sublimation. HPLC/ESI-MS: 99.6%, m/z=767 ($[M+H]^+$).

General Procedure for Fabrication of OLEDs

For the top emission OLED devices of example-1 to example-3 and of the comparative example a substrate with dimensions of 150 mm×150 mm×0.7 mm was ultrasonically cleaned with a 2% aquatic solution of Deconex FPD 211 for 7 minutes and then with pure water for 5 minutes, and dried for 15 minutes in a spin rinse dryer. Subsequently, Ag was deposited as anode at a pressure of 10-5 to 10-7 mbar.

Then, HT-1 and D-1 were vacuum co-deposited on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1.

Then, the ET-1 was vacuum deposited onto the emission layer to form the hole blocking layer (HBL). Then, the electron transport layer was formed on the hole blocking layer by co-depositing a compound of Formula (I) and LiQ in a wt % ratio of 1:1 for example-1 to example-3. For the comparative example the electron transport layer was formed on the hole blocking layer by co-depositing the compound comparative-1 and LiQ in a wt % ratio of 1:1.

Then, the electron injection layer is formed on the electron transporting layer by depositing Yb.

Ag:Mg is then evaporated at a rate of 0.01 to 1 Å/s at 10-7 mbar to form a cathode.

A cap layer of HT-1 is formed on the cathode.

The details of the layer stack in the top emission OLED devices are given below. A slash "/" separates individual layers. Layer thicknesses are given in squared brackets [ . . . ], mixing ratios in wt % given in round brackets ( . . . ):

Layer stack details:

Ag [100 nm]/HT-1:D-1 (wt % 92:8) [10 nm]/HT-1 [118 nm]/HT-2 [5 nm]/H09:BD200 (wt % 97:3) [20 nm]/ET-1 [5 nm]/Compound of Formula (I): LiQ (wt % 1:1) [31 nm]/Yb [2 nm]/Ag:Mg (wt % 90:10) [11 nm]/HT-1 [70 nm]

Technical Effect of the Invention

The OLED devices according to the invention show improved efficiency and lifetime at comparable voltage when using the compounds of Formula (I) in an electron transport layer instead of the comparative compound. The voltage stability is also improved.

List of Compounds Used

| | IUPAC name | Reference |
|---|---|---|
| HT-1 | N-([1,1'-biphenyl]-4-yl)-9,9-dimethyl-N-(4-(9-phenyl-9H-carbazol-3-yl)phenyl)-9H-fluoren-2-amine [CAS 1242056-42-3] | US2016322581 |
| HT-2 | N-(4-(dibenzo[b,d]furan-4-yl)phenyl)-N-(4-(9-phenyl-9H-fluoren-9-yl)phenyl)-[1,1'-bipheny]l]-4-amine [CAS 1824678-59-2] | WO2015174640 |
| D-1 | 4,4',4"-((1E,1'E,1"E)-cyclopropane-1,2,3-triylidenetris(cyanome-thanylylidene))tris(2,3,5,6-tetrafluorobenzonitrile) [CAS 1224447-88-4] | US2008265216 |
| HOST-1 | H09 (Fluorescent-blue host material) | Commercially available from Sun Fine Chemicals, Inc, S. Korea |
| EMITTER-1 | BD200 (Fluorescent-blue emitter material) | Commercially available from Sun Fine Chemicals, Inc, S. Korea |
| ET-1 | 2-(3'-(9,9-dimethyl-9H-fluoren-2-yl)-[1,1'-biphenyl]-3-yl)-4,6-diphenyl-1,3,5-triazine [CAS 1955543-57-3] | WO2016105141 |
| Comparative-1 | 2-(dibenzo[b,d]furan-3-yl)-4-(2',6'-diphenyl-[1,1':4',1"-terphenyl]-4-yl)-6-phenyl-1,3,5-triazine | — |
| LiQ | 8-Hydroxyquinolinolato-lithium [CAS 850918-68-2] | WO2013079217 |

TABLE 1

Properties of compounds M-1 to M-4 of Formula (I) and of comparative compound Comparative-1.

| | | mp [°C] | Tg [°C] | $T_{RO}$ [°C] |
|---|---|---|---|---|
| Comparative-1 | 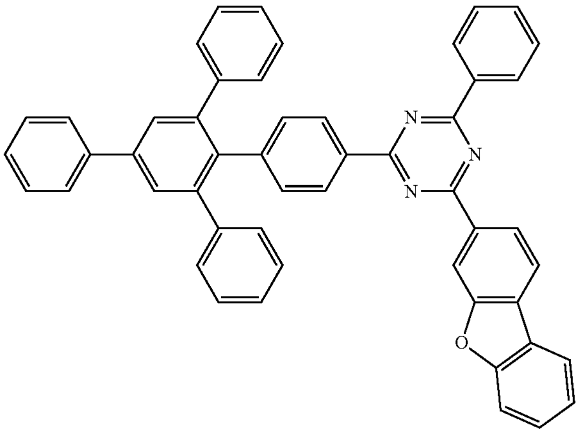 [SMILES: c1ccc(-c2cc(-c3ccccc3)c(-c3ccc(-c4nc(-c5ccccc5)nc(-c5ccc6c(c5)oc5ccccc56)n4)cc3)c(-c3ccccc3)c2)cc1] | 276 | 158 | 242 |

TABLE 1-continued
Properties of compounds M-1 to M-4 of Formula (I) and of comparative compound Comparative-1.
| | | mp [°C] | Tg [°C] | $T_{RO}$ [°C] |
|---|---|---|---|---|
| M-1 | 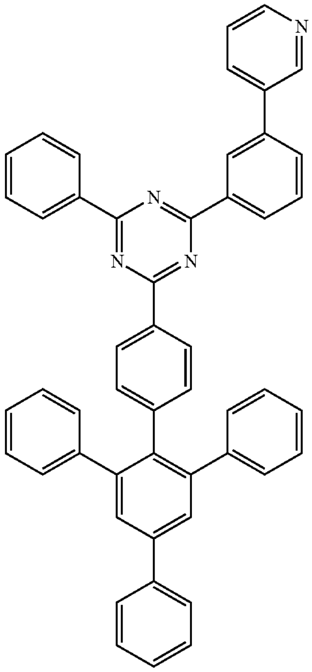 [SMILES: c1ccc(-c2cc(-c3ccccc3)c(-c3ccc(-c4nc(-c5ccccc5)nc(-c5cccc(-c6cccnc6)c5)n4)cc3)c(-c3ccccc3)c2)cc1] | — | 139 | 252 |
| M-2 | 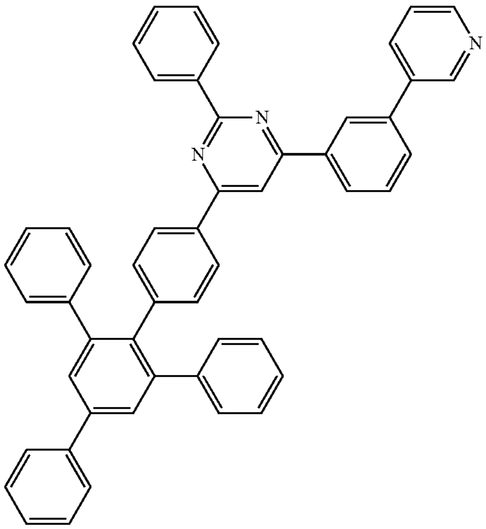 [SMILES: c1ccc(-c2cc(-c3ccccc3)c(-c3ccc(-c4cc(-c5cccc(-c6cccnc6)c5)nc(-c5ccccc5)n4)cc3)c(-c3ccccc3)c2)cc1] | 258 | 133 | 259 |

TABLE 1-continued

| Properties of compounds M-1 to M-4 of Formula (I) and of comparative compound Comparative-1. | | mp [°C] | Tg [°C] | $T_{RO}$ [°C] |
|---|---|---|---|---|
| M-3 | 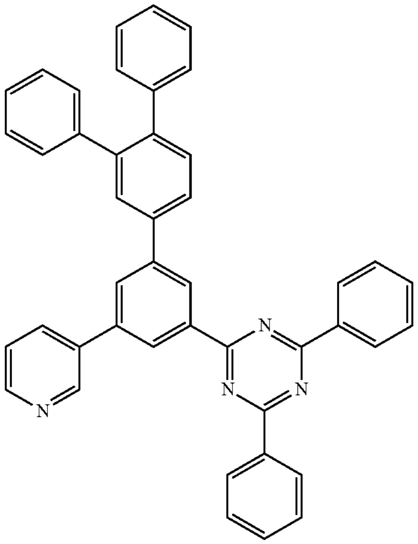 [SMILES: c1ccc(-c2nc(-c3ccccc3)nc(-c3cc(-c4cccnc4)cc(-c4ccc(-c5ccccc5)c(-c5ccccc5)c4)c3)n2)cc1] | 242 | 100 | 240 |
| M-4 | 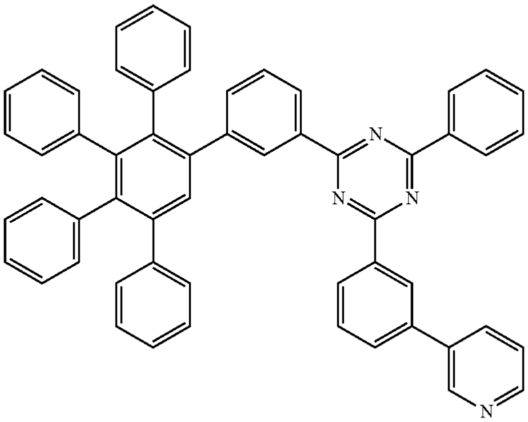 [SMILES: c1ccc(-c2nc(-c3cccc(-c4cccnc4)c3)nc(-c3cccc(-c4cc(-c5ccccc5)c(-c5ccccc5)c(-c5ccccc5)c4-c4ccccc4)c3)n2)cc1] | — | 139 | — |

TABLE 2

Dipole moment, HOMO and LUMO levels of compound comparative-1 and compounds of Formula (I) M-1 to M-4, simulated by DFT (B3LYP_Gaussian/6-31G*, gas phase)

| | Dipole moment [Debye] | HOMO [eV] | LUMO [eV] |
|---|---|---|---|
| Comparative-1 | 0.85 | −5.82 | −1.93 |
| M-1 | 2.69 | −5.86 | −1.92 |
| M-2 | 3.22 | −5.84 | −1.77 |
| M-3 | 2.46 | −5.87 | −1.92 |
| M-4 | 1.86 | −5.86 | −1.87 |

TABLE 3

Performance of an organic electroluminescent device comprising the compounds of Formula (I) or the comparative compound-1 as a matrix compound in the electron transport layer. CIE 1931 y = 0.045

| OLED device examples | Matrix compound | Additive | Operating voltage U at 10 mA/$cm^2$ (V) | CEff at 10 mA/$cm^2$ (cd/A) | LT97 at 30 mA/$cm^2$ (hours) | ΔU at 30 mA/$cm^2$ (V) |
|---|---|---|---|---|---|---|
| Comparative example | Compar-ative-1 | LiQ | 3.56 | 6.91 | 37 | 0.0605 |
| Example-1 | M-1 | LiQ | 3.53 | 7.24 | 51 | 0.0105 |
| Example-2 | M-2 | LiQ | 3.67 | 7.86 | 48 | 0.0035 |
| Example-3 | M-3 | LiQ | 3.68 | 7.25 | 82 | 0.0025 |

TABLE 4

| Examples of groups A with the bonding positions of the 6-membered ring comprising at least two N-atoms occupied by phenyl rings. | Calculated LUMO levels, simulated by DFT ($B_3$LYP_Gaussian/6-31G*, gas phase) in [eV] |
|---|---|
| 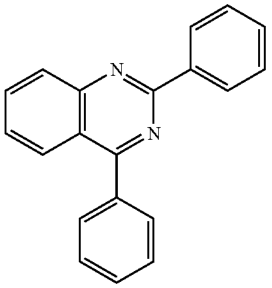 [SMILES: c1ccc(-c2nc(-c3ccccc3)c3ccccc3n2)cc1] | −1.87 |
| 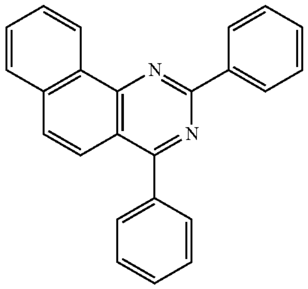 [SMILES: c1ccc(-c2nc(-c3ccccc3)c3ccc4ccccc4c3n2)cc1] | −1.77 |
| 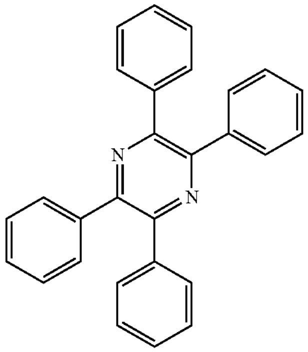 [SMILES: c1ccc(-c2nc(-c3ccccc3)c(-c3ccccc3)nc2-c2ccccc2)cc1] | −1.57 |
| 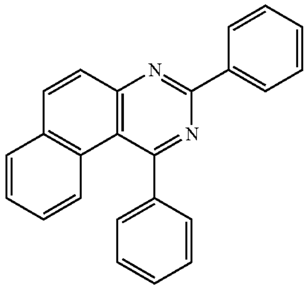 [SMILES: c1ccc(-c2nc(-c3ccccc3)c3c(ccc4ccccc43)n2)cc1] | −1.77 |
| 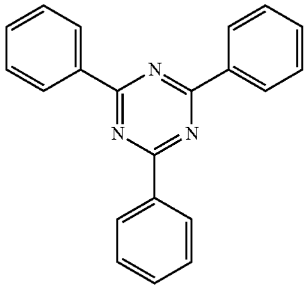 [SMILES: c1ccc(-c2nc(-c3ccccc3)nc(-c3ccccc3)n2)cc1] | −1.80 |

TABLE 4-continued

| Examples of groups A with the bonding positions of the 6-membered ring comprising at least two N-atoms occupied by phenyl rings. | Calculated LUMO levels, simulated by DFT ($B_3$LYP_Gaussian/6-31G*, gas phase) in [eV] |
|---|---|
| 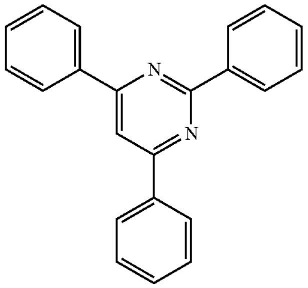 [SMILES: c1ccc(-c2cc(-c3ccccc3)nc(-c3ccccc3)n2)cc1] | −1.72 |
| 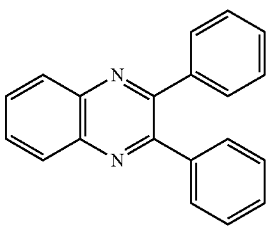 [SMILES: c1ccc(-c2nc3ccccc3nc2-c2ccccc2)cc1] | −1.90 |

The features disclosed in the foregoing description and in the dependent claims may, both separately and in any combination thereof, be material for realizing the aspects of the disclosure made in the independent claims, in diverse forms thereof.

The invention claimed is:

1. Compound having the general Formula (I)

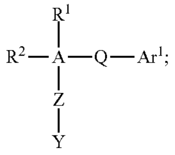

(I)

wherein

A is substituted or unsubstituted $C_3$ to $C_{14}$ heteroarylene comprising at least one six-membered ring, the six-membered ring comprising at least two N-atoms, wherein the one or more substituents, if present in the group A, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^1$, $R^2$, Q-$Ar^1$ and Z—Y are bound to C-atoms of A;

Q-$Ar^1$ and Z—Y are bound to C-atoms of the six-membered ring comprising at least two N-atoms of A;

$R^1$ is selected from the group consisting of H, substituted or unsubstituted $C_6$ to $C_{18}$ aryl, and substituted or unsubstituted $C_2$ to Cis heteroaryl, wherein the one or more substituents, if present in the group $R^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$R^2$ is selected from the group consisting of H, substituted or unsubstituted $C_6$ to $C_{18}$ aryl, and substituted or unsubstituted $C_2$ to $C_{18}$ heteroaryl, wherein the one or more substituents, if present in the group $R^2$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN; or is absent in case that A is $C_3$ heteroarylene;

Q represents a single bond between A and $Ar^1$ or is a group having the Formula (II)

(II)

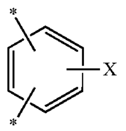

in Formula (II) the "*" symbols represent the positions for binding to A and $Ar^1$, respectively;

X is H, $C_1$ to $C_7$ alkyl or is represented by the general formula (IV)

(IV)

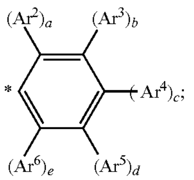

in formula (IV)

at least two of $Ar^2$ to $Ar^6$ are in ortho-position to each other; and/or at least one of $Ar^2$ and $Ar^6$ is in ortho-position to the *-position; or in case that a to e are 0 at the same time, X is in ortho-position to $Ar^1$;

$Ar^1$ is selected from the group consisting of CN-substituted phenyl and substituted or unsubstituted N-containing $C_3$ to $C_{20}$ heteroaryl, wherein the one or more substituents, if present in the group $Ar^1$, are independently selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

$Ar^1$ is different from A;

Z represents a single bond between A and Y or a group having the Formula (V)

(V)

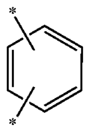

in Formula (V) the "*" symbols represent the positions for binding to A and Y, respectively;

Y is H, $C_1$ to $C_7$ alkyl or is represented by the general formula (VII)

(VII)

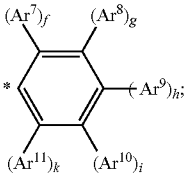

in formula (VII)

at least two of $Ar^7$ to $Ar^{11}$ are in ortho-position to each other; and/or at least one of $Ar^7$ and $Ar^{11}$ is in ortho-position to the *-position;

X and Y cannot be H and/or $C_1$ to $C_7$ alkyl at the same time;

Q and Y may be substituted with one or more substituents selected from the group consisting of $C_1$ to $C_7$ alkyl, $C_1$ to $C_7$ alkoxy, partially or perdeuterated $C_1$ to $C_7$ alkyl, partially or perdeuterated $C_1$ to $C_7$ alkoxy, partially or perfluorinated $C_1$ to $C_7$ alkyl, partially or perfluorinated $C_1$ to $C_7$ alkoxy, D, F and CN;

a to k are independently 0 or 1, provided that $2 \leq a+b+c+d+e+f+g+h+i+k \leq 5$;

$Ar^2$ to $Ar^{11}$ are independently selected from the group consisting of substituted or unsubstituted $C_6$ to $C_{12}$ aryl and $C_4$ to $C_{10}$ heteroaryl, wherein the one or more substituents, if present in one or more of the groups $Ar^2$ to $Ar^{11}$, are independently selected from the group consisting of $C_1$ to $C_6$ alkyl, $C_1$ to $C_6$ alkoxy, partially or perdeuterated $C_1$ to $C_6$ alkyl, partially or perdeuterated $C_1$ to $C_6$ alkoxy, partially or perfluorinated $C_1$ to $C_6$ alkyl, partially or perfluorinated $C_1$ to $C_6$ alkoxy, D, F and CN;

neither Formula (IV) nor Formula (VII) comprises condensed aromatic rings;

or a compound of having a structure selected from the following structures 13, 15, 16, 17, and 49 to 67

-continued
13
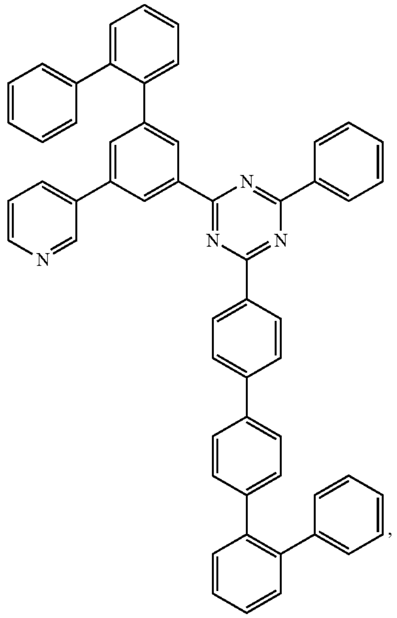
16
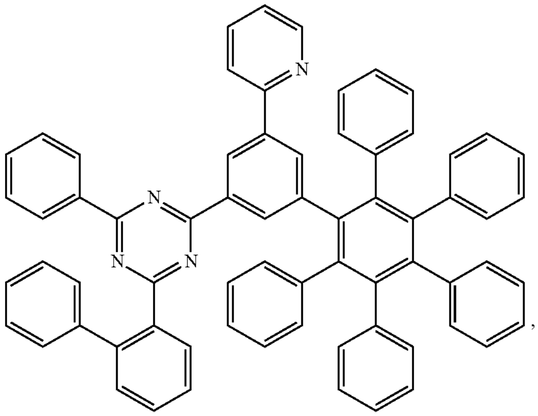
17
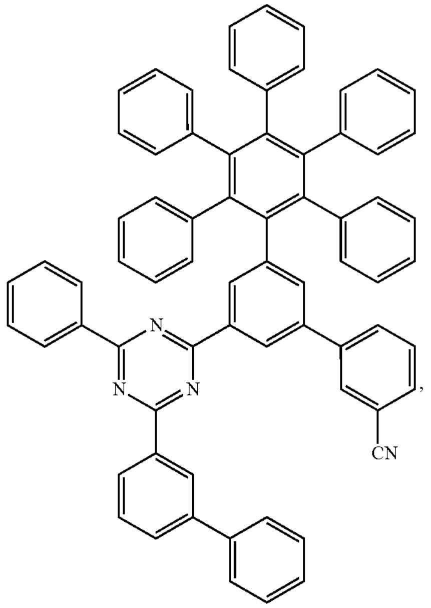
15
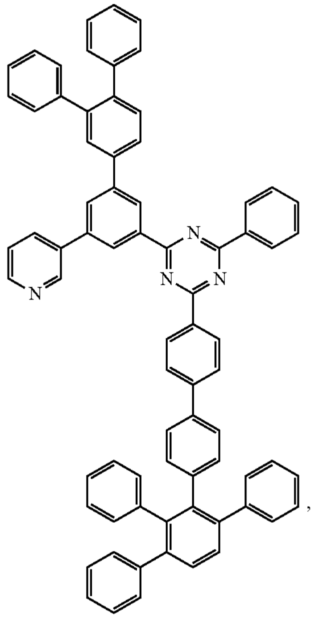
49
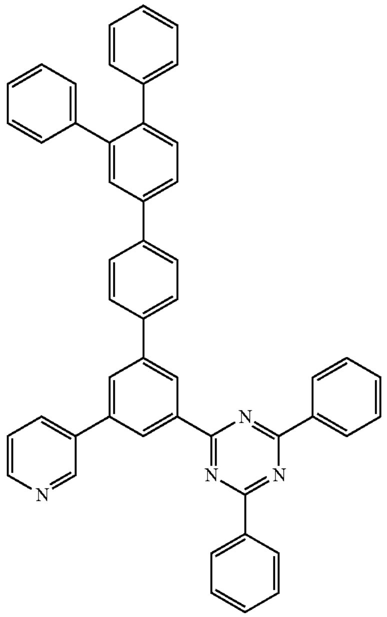

-continued
50
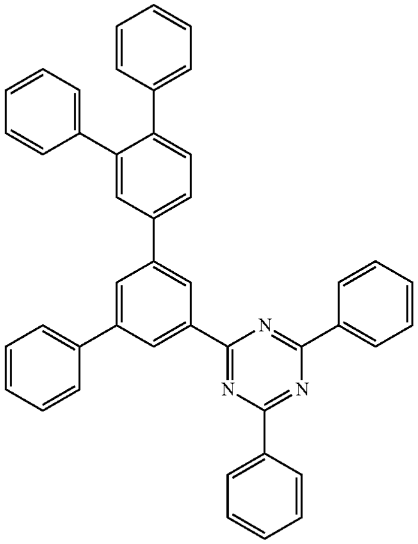
51
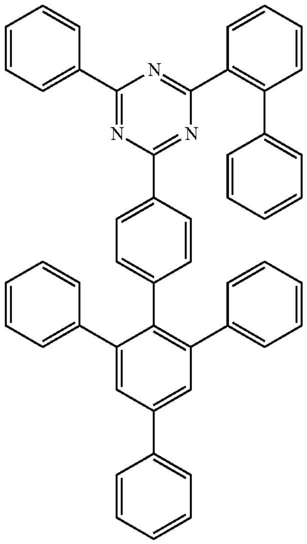
52
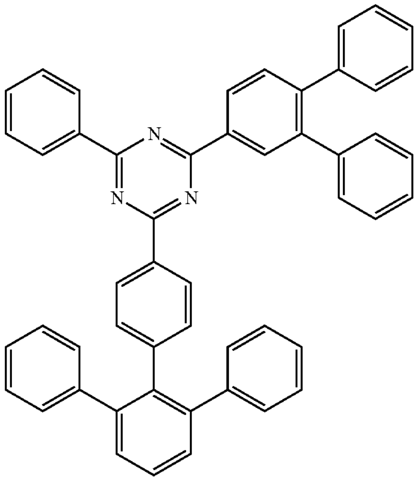
-continued
53
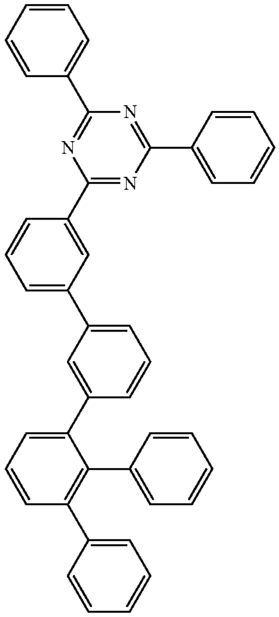
54
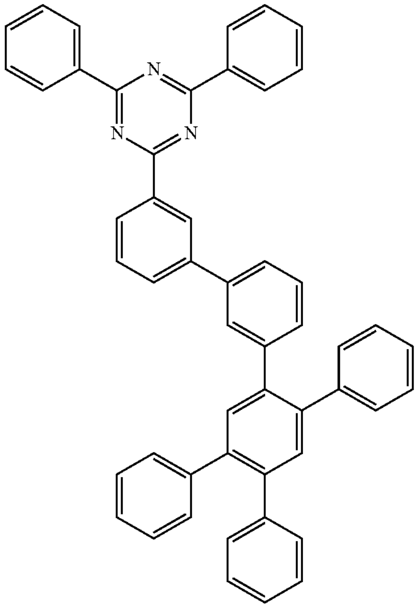

-continued
55
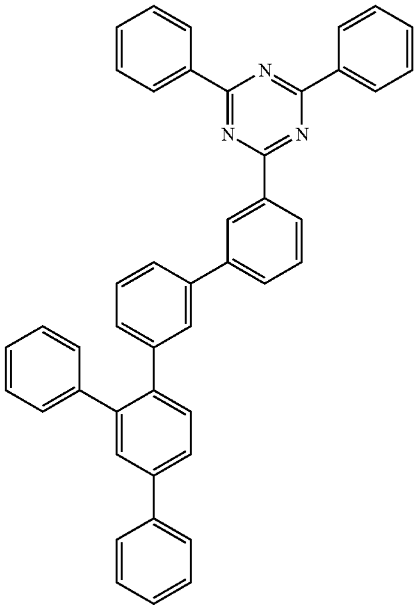
56
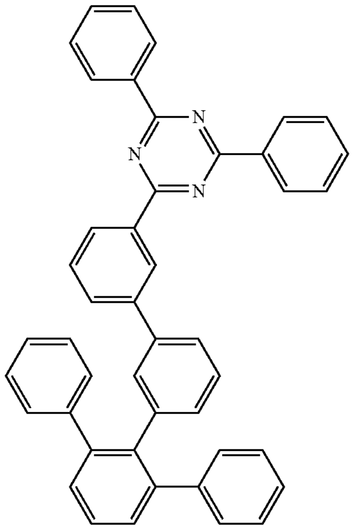
-continued
57
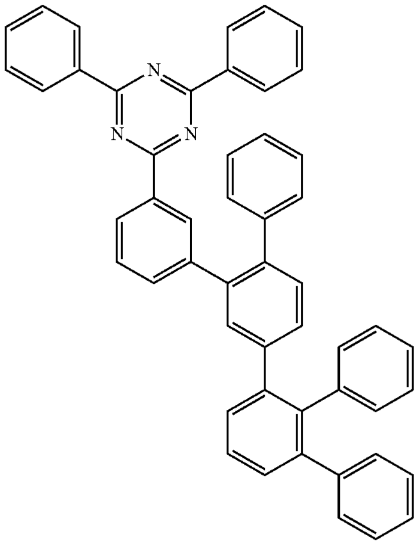
58
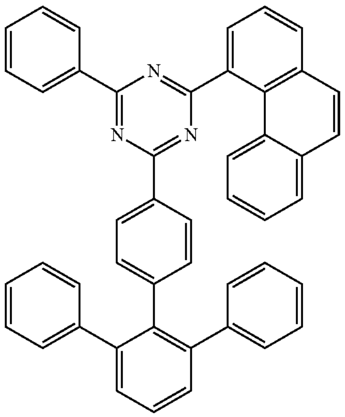
59
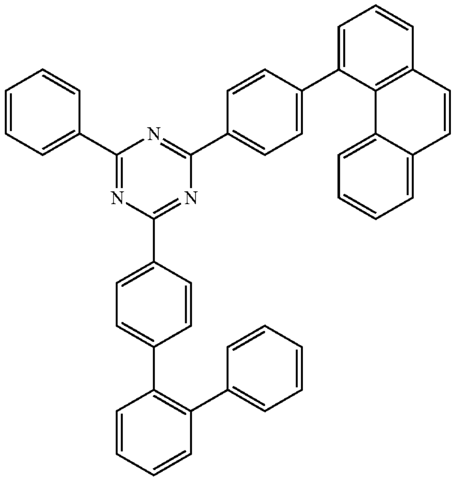

-continued
60
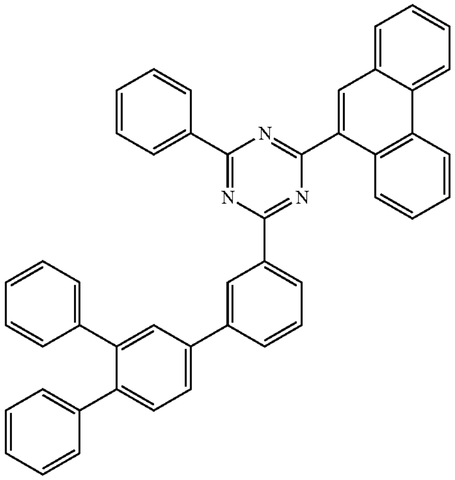
61
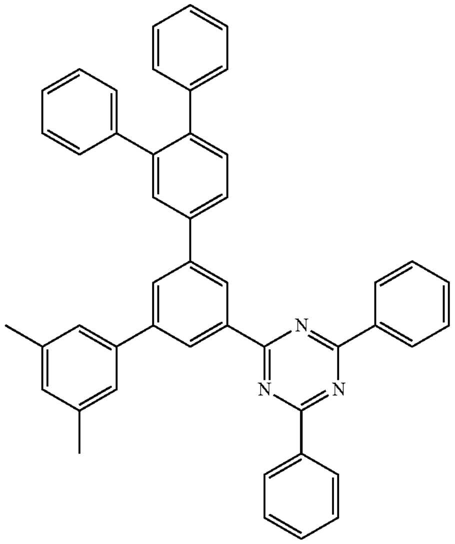
62
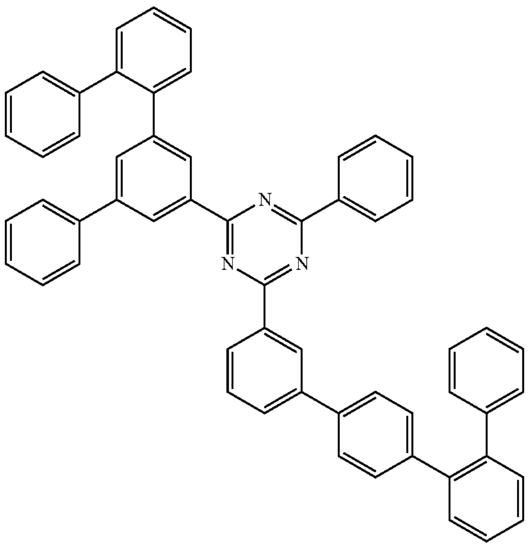
-continued
63
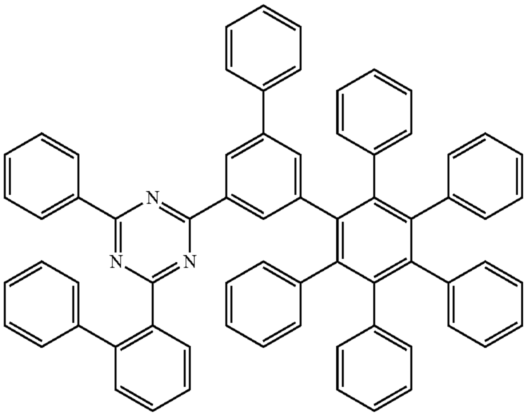
64
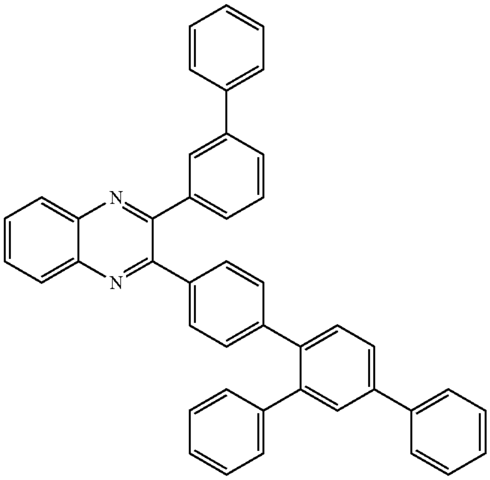
65
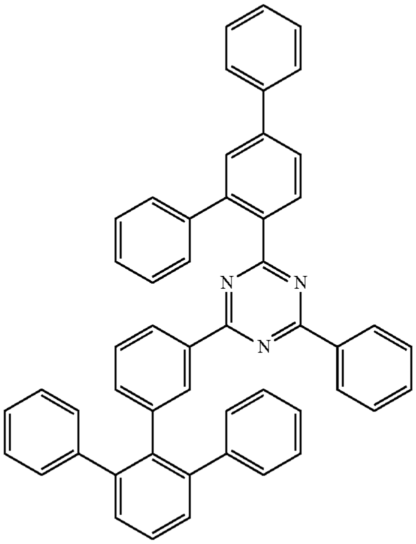

-continued

66

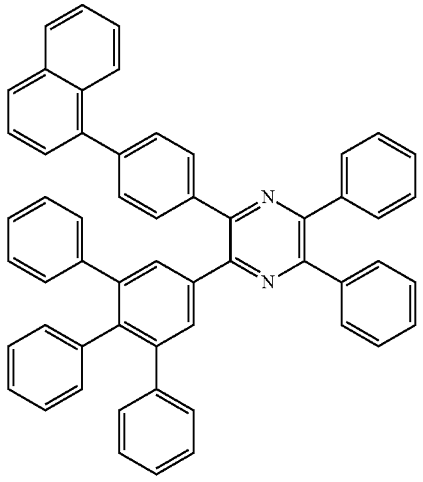

67

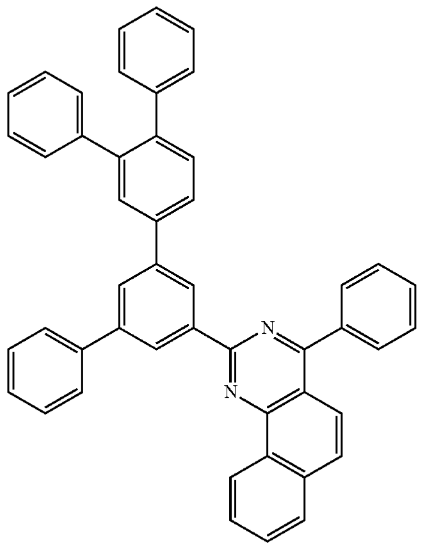

and a compound having the following formula is excluded

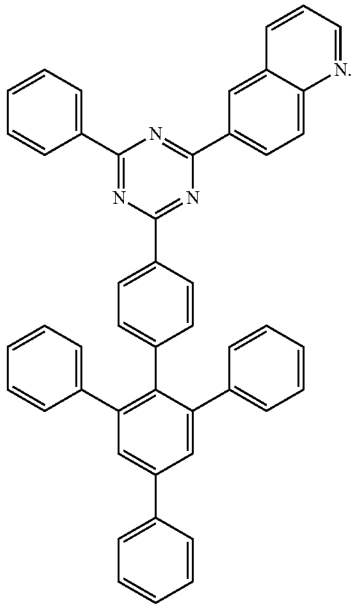 [SMILES: c1ccc(-c2cc(-c3ccccc3)c(-c3ccc(-c4nc(-c5ccccc5)nc(-c5ccc6ncccc6c5)n4)cc3)c(-c3ccccc3)c2)cc1]

2. Compound according to claim 1, wherein the 6-membered ring of A comprises 2 to 3 N-atoms.

3. Compound according to claim 1, wherein Q represents a group having the Formula (II) and/or Z represents a group having the Formula (v).

4. Compound according to claim 1, wherein Q represents a group having the Formula (II) and Z represents a group having the Formula (V).

5. Compound according to claim 1, wherein A is selected from the group consisting of triazinylene, pyrimidinylene, pyrazinylene, quinoxalinyl, quinazolinylene, and benzoquinazolinylene.

6. Compound according to claim 1, wherein $Ar^1$ is selected from the group consisting of pyridinyl, quinolinyl, isoquinolinyl, azaphenanthrenyl, carbazolyl, benzo-nitrilyl,

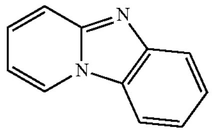, and 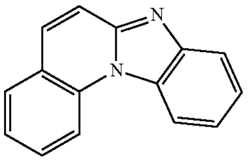.

7. Compound according to claim 1, wherein the total number of aromatic rings comprised in the compound of Formula (I) is from 7 to 14.

8. Organic semiconducting layer comprising the compound of Formula 1 according to claim 1.

9. Organic electronic device comprising the organic semiconducting layer according to claim 8, wherein the organic semiconducting layer is a charge generation layer.

10. Organic electronic device comprising the organic semiconducting layer according to claim 8, wherein the organic semiconducting layer is an electron transport layer and the electron transport layer comprises one or more additives, wherein the additive may be an n-type dopant.

11. Organic electronic device comprising the organic semiconducting layer according to claim 8, wherein the organic semiconducting layer is an electron transport layer and the electron transport layer consists of a compound of Formula 1.

12. Display device comprising the organic electronic device according to claim 9.

13. Lighting device comprising the organic electronic device according to claim 9.

* * * * *